US005958739A

United States Patent [19]
Mitchinson et al.

[11] Patent Number: 5,958,739
[45] Date of Patent: *Sep. 28, 1999

[54] MUTANT α-AMYLASE

[75] Inventors: Colin Mitchinson; Carol Requadt; Traci Ropp; Leif P. Solheim; Christopher Ringer; Anthony Day, all of Palo Alto, Calif.

[73] Assignee: Genencor International Inc., Rochester, N.Y.

[ * ] Notice: This patent is subject to a terminal disclaimer.

[21] Appl. No.: 08/704,706

[22] PCT Filed: Jun. 6, 1996

[86] PCT No.: PCT/US96/09089

§ 371 Date: Feb. 20, 1997

§ 102(e) Date: Feb. 20, 1997

[87] PCT Pub. No.: WO96/39528

PCT Pub. Date: Dec. 19, 1996

[51] Int. Cl.$^6$ ............... C12P 19/14; C12N 9/26; C12N 9/28; C07H 21/04
[52] U.S. Cl. ............... 435/99; 435/201; 435/202; 435/203; 435/204; 435/252.3; 435/252.31; 435/254.11; 435/320.1; 435/325; 435/410; 510/226; 510/300; 510/305; 510/320; 510/374; 510/392; 536/23.2
[58] Field of Search ............... 435/204, 320.1, 435/252.3, 99, 201, 202, 203, 252.31, 254.11, 325, 410; 510/226, 300, 305, 320, 37 A, 392; 536/23.2

[56] References Cited

U.S. PATENT DOCUMENTS

| | | | |
|---|---|---|---|
| Re. 34,606 | 5/1994 | Estell et al. | 510/392 |
| 4,261,868 | 4/1981 | Hora et al. | 510/393 |
| 4,284,722 | 8/1981 | Tamuri et al. | 435/94 |
| 4,493,893 | 1/1985 | Mielenz et al. | 435/91.41 |
| 4,620,936 | 11/1986 | Kielman et al. | 510/226 |
| 4,634,551 | 1/1987 | Burns et al. | 510/313 |
| 4,732,973 | 3/1988 | Barr et al. | 530/350 |
| 4,752,585 | 6/1988 | Koths et al. | 435/252.33 |
| 4,760,025 | 7/1988 | Estell et al. | 510/392 |
| 4,863,626 | 9/1989 | Coyne et al. | 510/530 |
| 5,118,623 | 6/1992 | Boguslawski et al. | 510/374 |
| 5,322,778 | 6/1994 | Antrim et al. | 435/99 |
| 5,346,823 | 9/1994 | Estell et al. | 435/222 |
| 5,364,782 | 11/1994 | Quax et al. | 435/202 |
| 5,736,499 | 4/1998 | Mitchinson et al. | 510/392 |
| 5,763,385 | 6/1998 | Bott et al. | 510/392 |

FOREIGN PATENT DOCUMENTS

| | | |
|---|---|---|
| 0946/92 | 7/1992 | Denmark . |
| 1503/92 | 12/1992 | Denmark . |
| 0 130 756 | 9/1985 | European Pat. Off. . |
| 0 208 491 | 1/1987 | European Pat. Off. . |
| 0 251 446 | 1/1988 | European Pat. Off. . |
| 0 273 268 | 7/1988 | European Pat. Off. . |
| 0 285 123 | 10/1988 | European Pat. Off. . |
| 0 378 261 | 7/1990 | European Pat. Off. . |
| 0 409 299 A2 | 1/1991 | European Pat. Off. . |
| 0 410 498 A2 | 1/1991 | European Pat. Off. . |
| 2 676 456 | 11/1992 | France . |
| 00353 | 1/1991 | WIPO . |
| WO 91/00353 | 1/1991 | WIPO . |
| WO 91/16423 | 10/1991 | WIPO . |
| WO 92/08778 | 5/1992 | WIPO . |
| 18314 | 8/1994 | WIPO . |
| 10603 | 4/1995 | WIPO . |
| 35382 | 12/1995 | WIPO . |
| 05295 | 2/1996 | WIPO . |

OTHER PUBLICATIONS

Joyet et al. (Dec. 1992 Hyperthermostable variants of a highly thermostable alpha–amylase. Biotechnology 10: 1579–1583.

Declerck et al. (Jun. 1995) Hyperthermostable mutants of Bacillus licheniformis alpha–amylase: multiple amino acid replacement and molecular modeling. Protein Engineering 8(10): 1029–1037.

Declerck et al. (Jun. 1990) Use of amber suppressors to investigate the thermostability of Bacillus licheniformis alpha–amylase. J. Biol. Chem. 265(26): 15481–15488.

Ngo et al. (Jun. 1994) Computational Complexity, Protein Structure Prediction, and the Levinthal Paradox. In: The Protein Folding Problem and Tertiary Structure Prediction. Eds. Merz et al. Birkhauser. Boston, MA. pp. 491–495.

Rudinger (Jun. 1976) Characteristics of the amino acids as components of a peptide hormone sequence. In: Peptide Hormones. Ed. J. A. Parsons. University Park Press. Baltimore, MD. pp. 1–7, Jun. 1976.

Bealin–Kelly et al., "Studies on the Thermostability of the α–amylase of *Bacillus caldovelox*," Appl Microbiol Biotechnol (1991) 36:332–336.

Bierbaum et al., "Production of protease with *Bacillus licheniformis* mutants insensitive to repression of exoenzyme biosynthesis," Appl Microbiol Biotechnol (1994) 40:611–617.

Boel et al., "Calcium Binding in α–Amylases: An X–ray Diffraction Study at 2.1–Å Resolution of Two Enzymes from Aspergillus," *Biochemistry* (1990) 29:6244–6249.

Bott et al., "the Three–dimensional Structure of Bacillus amyloliquefaciens Subtilisin at 1.8 Å and an Analysis of the Structural Consequences of Peroxide Inactivation," *J Biol Chem* (1988) 263:7895–7906.

Brady et al., "Solution of the Structure of *Aspergillus niger* Acid α–Amylase by Combined Molecular Replacement and Multiple Isomorphous Replacement Methods," *Acta Cryst* (1991) 47:527–535.

(List continued on next page.)

*Primary Examiner*—Robert A. Wax
*Assistant Examiner*—Einar Stole
*Attorney, Agent, or Firm*—Christopher L. Stone

[57] ABSTRACT

Novel α-amylase enzymes are disclosed in which one or more asparagine residues are substituted with a different amino acid or deleted. The disclosed α-amylase enzymes show altered or improved low pH starch hydrolysis performance, stability and activity profiles.

32 Claims, 17 Drawing Sheets

OTHER PUBLICATIONS

Brayer et al., "The structure of human pancreatic α–amylase at 1.8 Å resolution and comparisons with related enzymes," *Prot Science* (1995) 4:1730–1742.

Brosnan et al. "Investigation of the mechanisms of irreversible thermoinactivation of Bacillus stearothermophilus α–amylase," *Eur J Biochem* (1992) 203:225–231.

Burley et al., Aromatic–Aromatic Interaction: A Mechanism of Protein Structure Stabilization,: *Science* (1985) 229:23–28.

Byrne et al., "Energetic Contribution of side Chain Hydrogen Bonding to the Stability of Staphylococcal Nuclease," *Biochemistry* (1995) 34:13949–13960.

Chang et al., "Cyrstallization and Preliminary X–ray Crystallographic Analysis of α–Amylase from *Bacillus subtilis,*" *J Mol Biol* (1993) 229:235–238.

Chen et al., "Identification and elimination by site–directed mutagenesis of thermolabile aspartyl bonds in *Aspergillus awamore* glucoamylase," *Protein Engineering* (1995) 8:575–582.

Clarke et al., "Engineered Disulfide Bonds as Probes of the Folding Pathway of Barnase: Increasing the Stability of Proteins against the Rate of Denaturation," *Biochemistry* (1993) 32:4322–4329.

Dao–pin et al., "Contributions of Engineered Surface Salt Bridges to the Stability of T4 Lysozyme Determined by Directed Mutagenesis," *Biochemistry* (1991) 30:7142–7153.

Delboni et al., "Crystal structure of recombinant triosephosphate isomerase from *Bicillus stearothermophils*. An analysis of potential thermostability factors in six isomerases with known three–dimensional structures points to the improtance of hydrophobic interactions," *Protein Science* (1995) 4:2594–2604.

Doig et al., "N– and C–capping preferences for all 20 amino acids in α–helical peptides," *Protein Science* (1995) 4:1325–1336.

Eder et al., "Folding of Subtilisin BPN': Characterization of a Folding Intermediate," *Biochemistry* (1993) 32:18–26.

Eriksson et al., "Response of a Protein Structure to Cavity–Creating Mutations and its Relation to the Hydrophobic Effect," *Science* (1992) 255:178–183.

Estell et al. "Engineering an Enzyme by Site–directed Mutagenesis to be Resistant to Chemical Oxidation," *J Biol Chem* (1985) 260:6518–6521.

Fágáin, "Understanding and increasing protein stability," *Biochimica et Biophysica Acta* (1995) 1252:1–14.

Gong et al., "Hydrolysis of Cellulose: Mechanisms of Enzymatic and Acid Catalysis," Advances in Chemistry Series, American Chemical Society, Washington, D.C.(1979),pp. 261–287.

Gray et al., "Structural Genes Encoding the Thermophilic α–amylases of Bacillus stearothermophilus and Bacillus licheniformis," *J Bacteriol* (1986) 166:635–643.

Hahn et al., "Crystal Structure and Site–directed Mutagenesis of Bacillus macerans Endo–1,3–1,4– β–glucanase," *J Biol Chem* (1995) 270:3081–3088.

Hakansson et al., "Purification and Characterization of a Low Molecular Weight 1,4–β–Glucan Glucanohydrolase from the Cellulolytic Fungus Trichoderma Viride QM 9414," *Biochimica et Biophysica Acta* (1978) 524:385–392.

Holm et al., "Random mutagenesis used to probe the structure and function of Bacillus stearothermophilus alpha–amylase," *Prot. Engineering* (1990) 3:181–191.

Janecek et al., "α–Amylases and approaches leading to their enhanced stability," *FEBS* (1992) 304:1–3.

Janecek et al., "Evolution of Parallel β/α Barrel Enzyme Family Lightened by Structural Data on Starch–Processing Enzymes," *J Prot Chem* (1993) 12:509–514.

Janecek, "Sequence similarities and evolutionary relationships of microbial, plant and animal α–amylases," *Eur J Biochem* (1994) 224:519–524.

Janecek, "Sequence similarities in $(\alpha/\beta)_8$–barrel enzymes revealed by conserved regions of α–amylase," *FEBS* (1993) 316:23–26.

Janse et al., "Regional sequence homologies in starch–degrading enzymes," *Curr Genet* (1993) 24:400–407.

Jespersen et al., "Starch– and Glycogen–Debranching and Branching Enzymes: Prediction of Structural Features of the Catalytic $(\alpha/\beta)_8$–Barrel Domain and Evolutionary Relationship to Other Amylolytic Enzymes," *J Prot Chem* (1993) 12:791–805.

Jorgensen et al., "Cloning of a chromosomal α–amylase gene from *Bacillus stearothermophilus,*" *FEMS Microbiol Letters* (1991) 77:271–276.

Kadziola et al. "Crystal and Molecular Structure of Barley α–Amylase," *J Mol Biol* (1994) 239:104–121.

Kellis Jr. et al., "Contribution of hydrophobic interactions to protein stability," *Nature* (1988) 333:784–786.

Kidd et al., "A Weak Calcium Binding Site in Subtilisin BPN' has a Dramatic Effect on Protein Stability," *J. Am. Chem. Soc.* (1996) 118:1645–1650.

Kim et al., "Changes in Optimum pH and Thermostability of α–amylase from *Bacillus licheniformis* by Site–directed Mutagenesis of His 235 and Asp 328," *Bull. Korean Chem. Soc.* (1994) 15:832–835.

Larson et al., "Refined Molecular Structure of Pig Pancreatic α–Amylase at 2–1 Å Resolution," *J Mol Biol* (1994) 235:1560–1584.

Lehmann et al., "Differential chemical modification of substrate binding areas in porcine–pancreatic alph–amylase by three regioisomeric photolabile ligands," *Carbohydrate Research* (1994) 265:19–30.

MacGregor et al., "Relationships between Structure and Activity in the α–Amylase Family of Starch–metabolising Enzymes," *Starch* (1993) 45:232–237.

Machius et al., "Crystal Structure of Calcium–depleted Bacillus licheniformis α–amylase at 2.2 Å Resolution," *J Mol Biol* (1995) 246:545–559.

Malcolm et al., "Ancestral lysozymes reconstructed, neutrality tested, and thermostability linked to hydrocarbon packing," *Nature* (1990) 345:86–89.

Manning et al., "Thermostable α–amylase of Bacillus stearothermophilus," *J Biol Chem* (1961) 236:2952–2965.

Matsui et al., "A mutant α–amylase with enhanced activity specific for short substrates," *FEBS* (1992) 310:216–218.

Matsui et al., "An increase in the transglycosylation activity of Saccharomycopsis α–amylase altered by site–directed mutagenesis," *Biochimica et Biophysica Acta* (1991) 1077:416–419.

Matsui et al., "Roles of the Aromatic Residues Conserved in the Active Center of Saccharomycopsis α–Amylase for Transgylcosylation and Hydrolysis Activity," *Biochem* (1994) 33:451–458.

Matsuura et al., "Structure and Possible Catalytic Residues of Taka–Amylase A," *J Biochem* (1984) 95:697–702.

Matthews et al., "Solvent Content of Protein Crystals," *J Mol Biol* (1968) 33:491–497.

Matthews, "Structural and Genetic Analysis of Protein Stability," *Annu. Rev. Biochem.* (1993) 62:139–160.

Mazur et al., "The Catalytic Mechanism of α–Amylase Based Upon Enzyme Crystal Structures and Model Building Calculations," *Biochem Biophys Res Com* (1994) 204:297–302.

Mecham et al., "Trypsin–Like Neutral Protease Associated with Soluble Elastin," *Biochem* (1977) 16:3825–3831.

Mitchinson et al., "Protein Engineering of Disulfide Bonds in Subtilisin BPN'," *Biochemistry* (1989) 28:4807–4815.

Mizuno et al., "Crystallization and Preliminary X–ray Studies of Wild Type and Catalytic–site Mutant α–Amylase from bacillus subtilis," *J Mol Biol* (1993) 234:1282–1283.

Mosimann et al. "A Critical Assessment of Comparative Molecular Modeling of Tertiary Structures of Proteins," *Prot* (1995) 23:301–317.

Moult et al., "A Large–Scale Experiment to Assess Protein Structure Prediction Methods," *Prot* (1995) 23:ii–iv.

Muir et al., "Citrate synthase from the hyperthermophilic Archaeon, *Pyrococcus furiosus,*" *Protein Engineering* (1995) 8:583–592.

Nakajima et al., "Nucleotide Sequence of the *Bacillus stearothermophilus* α–Amylase Gene," *J Bacteriol* (1985) 163:401–406.

Nakatani et al., "Effect of Modifying histidine residues on the action of Bacillus amyloliquefaciens and barley–malt α–amylases," *Carbohydrate Research* (1994) 257:155–161.

Nicholson et al., "Enhanced protein thermostability from designed mutations that interact with α–helix dipoles," *Nature* (1988) 336:651–656.

Ogasahara et al., Studies on Thermophilic α–Amylase from *Bacillus stearothermophilus*, section I, *J Biochem* 67:65–75. (1970).

Ogasahara et al., Studies on Thermophilic α–Amylase from *Bacillus stearothermophilus*, section II, *J Biochem* 67:76–82. (1970).

Ottesen et al., "The Subtilisins," *Methods in Enzymology* Chapter 11 pp. 199–215.

Pantoliano et al., "The Engineering of Binding Affinity at Metal Ion Binding Sites for the Stabilization of Proteins: Subtilisin as a Test Case," *Biochemistry* (1988) 27:8311–8317.

Perry et al., "Disulfide Bond Engineered into T4 Lysozyme: Stabilization of the Protein Toward Thermal Inactivation," *Science* (1984) 226:555–557.

Qian et al., "Structure and Molecular Model Refinement of Pig Pancreatic α–Amylase at 2–1 Å Resolution," *J Mol Biol* (1993) 231:785–799.

Qian et al., "The Active Center of a Mammalian α–Amylase. Structure of the Complex of a Pancreatic α–Amylase with a Carbohydrate Inhibitor Refined to 2.2 Å Resolution," *Biochem* (1994) 33:6284–6294.

Ramasubbu et al., "Crystallization and Preliminary X–Ray Diffraction Studies of Human Salivary α–amylase," *Prot* (1991) 11:230–232.

Richardson et al., "Amino Acid Preferences for Specific Locations at the Ends of α Helices," *Science* (1988) 240:1648–1652.

Russell et al., "Engineering thermostability: lessons from thermophilic proteins," *Current Opinion in Biotechnology* (1995) 6:370–374.

Samudrala et al., "Confronting the Problem of Interconnected Structural Changes in the Comparative Modeling of Proteins," *Prot* (1995) 23:327–336.

Shih et al., "Design and structural analysis of an engineered thermostable chicken lysozyme," *Protein Science* (1995) 4:2063–2072.

Siezen et al., "Homology modelling and protein engineering strategy of subtilases, the family of subtilisin–like serine proteinases," (1991) 719–737.

Sogaard et al., "α–Amylases: Structure and function," *Carbohydrate Polymers* (1993) 21:137–146.

Sogaard et al., "Site–directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley α–amylase 1," *J Biol Chem* (1993) 268:22480–22484.

Staberg, "Cellulases—The enzymes," Ph.D. Thesis—Uppsala University pp. 16–18.

Strausberg et al., "Directed Evolution of a Subtilisin with Calcium–Independent Stability," *Bio/Technology* (1995) 13:669–672.

Strokopytov et al., "X–ray Structure of Cyclodextrin Glycosyltransferase Complexed with Acarbose. Implications for the Catalytic Mechanism of Glycosidases," *Biochem* (1995) 34:2234–2240.

Suzuki et al. "Crystallization and Preliminary Crystallographic Study of Bacterial α–Amylases," *J Biochem* (1990) 108:379–381.

Suzuki et al., "Amino Acid Residues Stabilizing a Bacillus α–Amylase against Irreversible Thermoinactivation," *J Biol Chem* (1989) 264:18933–18938.

Svendsen, "Chemical Modifications of the Subtilisins with Special Reference to the Binding of Large Substrates. A Review." *Review: Carlsberg Res. Commun* (1976) 41:237–291.

Svensson et al., "Mutational analysis of glycosylase function," *J Biotech* (1993) 29:1–37.

Svensson, "Protein engineering in the α–amylase family: catalytic mechanism, substrate specificity, and stability," *Plant Mol Biol* (1994) 25:141–157.

Swift et al., "Structure and Molecular Model Refinement of *Aspergillus oryzae* (TAKA) α–Amylase: an Application of the Simulated–Annealing Method," *Acta Cryst* (1991) 47:544–548.

Szilágyi et al., "Structural basis for the extreme thermostability of D–glyceraldehyde–3–phosphate dehydrogenase form *Thermotoga maritima*: analysis based on homology modelling," *Protein Engineering* (1995) 8:779–789.

Takase et al., "Site–directed mutagenesis of active site residues in *Bacillus subtilis* α–amylase," *Biochemica et Biophysica Acta* (1992) 1120:281–288.

Tanner et al., "Determinants of Enzyme Thermostability Observed in the Molecular Structure of *Thermus acquaticus* D–Glyceraldehyde–3–phosphate Dehydrogenase at 2.5 Å Resolution," *Biochemistry* (1996) 35:2597–2609.

Tomazic et al., "Why is One Bacillus α–Amylase More Resistant against Irreversible Thermoinactivation than Another?" *J Biol Chem* (1988) 263:3092–3096.

Tomazic et al., "Mechanisms of Irreversible Thermal Inactivation of Bacillus α–Amylases" *J. of Biol. Chem.* 292(7):3086–3091 (Mar. 1988).

Ulker et al., "Production and characterization of an unglycosilated low molecular weight 1, 4–β–glucan–glucanohydrolase of *Trichoderma reesei,*" *Trichoderma reesei cellulases*, Ch. 5 pp. 60–77.

Vallee et al., "Characterization, Crystallization and Preliminary X-ray Crystallographic Analysis of the Complex between Barley α-Amylase and the Bifunctional α-Amylase/Subtilisin Inhibitor from Barley Seeds," *J Mol Biol* (1994) 236:368–371.

Vallee et al., "Metal Content of α-Amylases of Various Origins," *Journal of Biological Chemistry* (1959) 234:2901–2905.

Vihinen et al., "C-terminal truncations of a thermostable *Bacillus stearothermophilus* α-amylase," *Prot Engineering* (1994) 7:1255–1259.

Vihinen et al., "Site-Directed Mutagenesis of a Thermostable α-Amylase from Bacillus stearothermophilus: Putative Role of Three Conserved Residues," *J Biochem* (1990) 107:267–272.

von der Osten et al., "Protein engineering of subtilisins to improve stability in detergent formulations," *J Biochem* (1993) 28:55–68.

Walter et al., "Destabilization of a Protein Helix by Electrostatic Interactions," *J. Mol. Biol.* (1995) 252:133–143.

Warren et al., "Composition analysis of α-helices in thermophilic organisms," *Protein Engineering* (1995) 8:905–913.

Watanabe et al., "Multiple proline substitutions cumulatively thermostabilize *Bacillus cereus* ATCC7064 oligo-1, 6-glucosidase," *Eur. J. Biochem.* (1994) 226:277–283.

Wells et al., "In Vivo Formation and Stability of Engineered Disulfide Bonds in Subtilisin,"*The Journal of Biological Chemistry* (1986) 261:6564–6570.

Yeong Lee et al., "Crystallization and a Preliminary X-Ray Crystallographic Study of α-Amylase from Bacillus licheniformis," *Arch Biochem Biophys* (1991) 291:255–257.

Zhu et al., "Phospholipase $A_2$ Engineering. The Roles of Disulfide Bonds in Structure, Conformational Stability, and Catalytic Function," *Biochemistry* (1995) 34:15307–15314.

Zuber, "Temperature adaptation of lactate dehydrogenase Structural, functional and genetic aspects," *Biophysical Chemistry* (1988) 29:171–1793.

N188T 5'-G GAT TGG GAA GTG TCG ACT GAA AAC GGC AAC TAT GAT-3' (SEQ ID NO:4)
                            SalI

N188P 5'-G GAT TGG GAA GTT TCC CCA GAA AAT GGC AAC TAT GAT-3' (SEQ ID NO:5)
                                     pflMI N188R 5'-G GAT TGG GAA GTT TCT AGA GAA AAC GGC AAC TAT GAT-3' (SEQ ID NO:6)
                                XbaI N188L 5'-G GAT TGG GAA GTT TCC CTC GAG AAC GGC AAC TAT GAT-3' (SEQ ID NO:7)
                                    XhoI N188A 5'-G GAT TGG GAA GTT TCG GCC GAA AAC GGC AAC TAT GAT-3' (SEQ ID NO:8)
                                   EagI N188G 5'-G GAT TGG GAA GTT TCC GGA GAA AAC GGC AAC TAT GAT-3' (SEQ ID NO:9)
                                    BspEI N188V 5'-G GAT TGG GAA GTT AGC GTC GAA AAC GGC AAC TAT GAT-3' (SEQ ID NO:10)
                                    HgaI N188K 5'-G GAT TGG GAA GTT TCC AAG GAA AAC GGC AAC TAT GAT-3' (SEQ ID NO:11)
                                    StyI N188Q 5'-G GAT TGG GAA GTT TCC CAG GAA AAT GGC AAC TAT GAT-3' (SEQ ID NO:12)
                                          BstXI N188H 5'-G GAT TGG GAA GTT TCT CAT GAA AAC GGC AAC TAT GAT-3' (SEQ ID NO:13)
                                   BspHI

FIG._1A

N188E 5'-G GAT TGG GAA GTT TCC GAA GAG AAC GGC AAC TAT GAT-3' (SEQ ID NO:14)

N188D 5'-G GAT TGG GAA GTT TCC GAG GAG AAC GGC AAC TAT GAT-3' (SEQ ID NO:15)
              BseRI

N188Y 5'-G GAT TGG GAA GTT TCA TAT GAA AAC GGC AAC TAT GAT-3' (SEQ ID NO:16)
              NdeI

N188C 5'-G GAT TGG GAA GTC TCC TGC GAA AAC GGC AAC TAT GAT-3' (SEQ ID NO:17)
         BsmAI

N188F 5'-G GAT TGG GAA GTT TCC TTC GAA AAC GGC AAC TAT GAT-3' (SEQ ID NO:18)
              BstBI

N188I 5'-G GAT TGG GAA GTT TCG ATC GAA AAC GGC AAC TAT GAT-3' (SEQ ID NO:19)
              PvuI

N188M 5'-G GAT TGG GAA GTT TCC ATG GAA AAC GGC AAC TAT GAT-3' (SEQ ID NO:20)

N188W 5'-G GAT TGG GAA GTT TCC TGG GAA AAC GGC AAC TAT GAT-3' (SEQ ID NO:21)
              BstNI

N188S 5'-G GAT TGG GAA GTG AGC TCT GAA AAC GGC AAC TAT GAT-3' (SEQ ID NO:22)
         SstI

FIG._1B

| | | |
|---|---|---|
| PCR A+ | 5'-AGG AAA GGC TTG GGA TTG GGA AGT-3' (179) | (SEQ ID NO:23) |
| PCR A− | 5'-ACT TCC CAA TCC CAA GCC TTT CCT-3' (179) | (SEQ ID NO:24) |
| PCR B+ | 5'-GGC AAC TAT GAT TAT TTG ATG TAT-3' (191) | (SEQ ID NO:25) |
| PCR B− | 5'-ATA CAT CAA ATA ATC ATA GTT GCC-3' (191) | (SEQ ID NO:26) |
| PCR LAAfs5 | 5'-CTT CAT TCC CGC GAC ATT AAC-3' (90) | (SEQ ID NO:27) |
| PCR ClaI-SalI | 5'-GA TTC CCT TGT GAG AAT AAA AG-3' (356) | (SEQ ID NO:28) |
| PCR I+ | 5'-AAT CAT GTC AGG GAA AAA ACT GGG-3' (246) Bsrl | (SEQ ID NO:29) |
| PCR I− | 5'-CCC AGT TTT TTC CCT GAC ATG ATT-3' (246) Bsrl | (SEQ ID NO:30) |
| PCR J+ | 5'-TTT ACG GTA GCT GAA TAT TGG CAG-3' (257) | (SEQ ID NO:31) |
| PCR J− | 5'-CTG CCA ATA TTC AGC TAC CGT AAA-3' (257) | (SEQ ID NO:32) |

FIG._2

```
AGCTTGAAGA AGTGAAGAAG CAGAGAGGCT ATTGAATAAA TGAGTAGAAA GCGCCATATC    60

GGCGCTTTTC TTTTGGAAGA AAATATAGGG AAAATGGTAC TTGTTAAAAA TTCGGAATAT   120

TTATACAACA TCATATGTTT CACATTGAAA GGGGAGGAGA ATCATGAAAC AACAAAAACG   180
                                              M  K  Q  Q  K  R

GCTTTACGCC CGATTGCTGA CGCTGTTATT TGCGCTCATC TTCTTGCTGC CTCATTCTGC   240
 L  Y  A   R  L  L  T   A  L  I  F   L  L  P   H  S  A

AGCAGCGGCG GCAAATCTTA ATGGGACGCT GATGCAGTAT TTTGAATGGT ACATGCCCAA   300
 A  A  A   A  N  L  N   G  T  L   M  Q  Y   F  E  W  Y   M  P  N

TGACGGCCAA CATTGGAAGC GTTTGCAAAA CGACTCGGCA TATTTGGCTG AACACGGTAT   360
 D  G  Q   H  W  K  R   L  Q  N   D  S  A   Y  L  A  E   H  G  I

TACTGCCGTC TGGATTCCCC CGGCATATAA GGGAACGAGC CAAGCGGATG TGGGCTACGG   420
 T  A  V   W  I  P  P   A  Y  K   G  T  S   Q  A  D  V   G  Y  G

TGCTTACGAC CTTTATGATT TAGGGGAGTT TCATCAAAAA GGGACGGTTC GGACAAAGTA   480
 A  Y  D   L  Y  D  L   G  E  F   H  Q  K   G  T  V  R   T  K  Y

CGGCACAAAA GGAGAGCTGC AATCTGCGAT CAAAAGTCTT CATTCCCGCG ACATTAACGT   540
 G  T  K   G  E  L  Q   S  A  I   K  S  L   H  S  R  D   I  N  V

TTACGGGGAT GTGGTCATCA ACCACAAAGG CGGCGCTGAT GCCACCGAAG ATGTAACCGC   600
 Y  G  D   V  V  I  N   H  K  G   A  D  A   T  E  D   V  T  A

GGTTGAAGTC GATCCCGCTG ACCGCAACCG CGTAATTTCA GGAGAACACC TAATTAAAGC   660
 V  E  V   D  P  A  D   R  N  R   V  I  S   G  E  H  L   I  K  A
```

FIG._3A

```
CTGGACACAT TTTCATTTTC CGGGGCGCGG CAGCACATAC AGCGATTTTA AATGGCATTG   720
 W  T  H    F  H  F  P    G  R  G    S  T  Y    S  D  F  K    W  H  W

GTACCATTTT GACGGAACCG ATTGGGACGA GTCCCGAAAG CTGAACCGCA TCTATAAGTT   780
 Y  H  F    D  G  T  D    I  G  T  D    V  P  K    L  N  R  I    Y  K  F

TCAAGGAAAG GCTTGGGATT GGGAAGTTTC CAATGAAAAC GGCAACTATG ATTATTGAT   840
 Q  G  K    A  W  D  W    G  E  V  S    N  E  N    G  N  Y  D    Y  L  M

GTATGCCGAC ATCGATTATG ACCATCCTGA TGTCGCAGCA GAAATTAAGA GATGGGCAC    900
 Y  A  D    I  D  Y  D    H  P  D    V  A  A    E  I  K  R    W  G  T

TTGGTATGCC AATGAACTGC AATTGGACGG TTTCCGTCTT GATGCTGTCA AACACATTAA   960
 W  Y  A    N  E  L  Q    L  D  G    F  R  L    D  A  V  K    H  I  K

ATTTTCTTTT TTGCGGGATT GGGTTAATCA TGTCAGGGAA AAAACGGGGA AGGAAATGTT  1020
 F  S  F    L  R  D  W    V  N  H    V  R  E    K  T  G  K    E  M  F

TACGGTAGCT GAATATTGGC AGAATGACTT GCTTCATTAT CAGTTCCATG CTGCATCGAC  1080
 T  V  A    E  Y  W  Q    N  D  L    L  H  Y    Q  F  H  A    A  S  T

AAATTTAAT CATTCAGTGT TTGACGTGCC GCTGAACGGT GAAAACTATT CCAAGCATCC  1140
 N  F  N    H  S  V  F    D  V  P    L  N  G    E  N  Y  L    K  H  P

ACAGGGAGGC GGCTATGATA TGAGGAAATT GAATACACAG ACGGTCGTTT CGCTTGAGTC  1200
 Q  G  G    G  Y  D  M    R  K  L    N  G    T  V  V  S    K  H  P

GTTGAAATCG GTTACATTTG TCGATAACCA TGATACACAG CCGGGGCAAT CGCTTGAGTC  1260
 L  K  S    V  T  F  V    D  N  H    D  T  Q    P  G  Q  S    L  E  S

GACTGTCCAA ACATGGTTTA AGCCGCTTGC TTACGCTTTT ATTCTCACAA GGGAATCTGG  1320
 T  V  Q    T  W  F  K    P  L  A    Y  A  F    I  L  T  R    E  S  G

FIG._3B
```

```
ATACCCTCAG GTTTTCTACG GGGATATGTA CGGGACGAAA GGAGACTCCC AGCGCGAAAT    1380
 Y  P  Q    V  F  Y  G   D  M  Y    G  T  K    G  D  S  Q   R  E  I
TCCTGCCTTG AAACACAAAA TTGAACCGAT CTTAAAAGCG AGAAAACAGT ATGCGTACGG    1440
 P  A  L    K  H  K  I   E  P  I    L  K  A    R  K  Q  Y   A  Y  G
AGCACAGCAT GATTATTTCG ACCACCATGA CATTGTCGGC TGGACAAGGG AAGGCGACAG    1500
 A  Q  H    D  Y  F  D   H  H  D    I  V  G    W  T  R  E   G  D  S
CTCGGTTGCA AATTCAGGTT TGGCGGCATT AATAACAGAC GGACCCGGTG GGGCAAAGCG    1560
 S  V  A    N  S  G  L   A  A  L    I  T  D    G  P  G  G   A  K  R
AATGTATGTC GGCCGGCAAA ACGCCGGTGA GACATGGCAT GGGAGAGTTT GAAACCGTTC    1620
 M  Y  V    G  R  Q  N   A  G  E    T  W  H    G  E  F    N  R  S
GGAGCCGGTT GTCATCAATT CGGAAGGCTG AGAAGAGCAG TTTCCTGAAG GCGGGTCGGT    1680
 E  P  V    V  I  N  S   E  G  W    R  R  S    F  L  K    G  G  S  V
TTCAATTTAT GTTCAAAGAT AGAAGAGCGA TGATTACATT TTATAATTAA GAAATCCGTT    1740
 S  I  Y    V  Q  R  *
TTTTTATTTT GCCCGTCTTA TAAATTTCTT TGATTACATT TTATAATTAA TTTTAACAAA    1800
GTGTCATCAG CCCTCAGGAA GGACTTGCTG ACAGTTTGAA TCGCATAGGT AAGGCGGGGA    1860
TGAAATGGCA ACGTTATCTG ATGTAGCAAA GAAAGCAAAT GTGTCGAAAA TGACGGTATC    1920
GCGGGTGATC AATCATCCTG AGACTGTGAC GGATGAATTG AAAAAGCT               1968
```

FIG._3C

```
ANLNGTLMQY FEWYMPNDGQ HWKRLQNDSA YLAEHGITAV WIPPAYKGTS QADVGYGAYD    60
LYDLGEFHQK GTVRTKYGTK GELQSAIKSL HSRDINVYGD VVINHKGGAD ATEDVTAVEV   120
DPADRNRVIS GEHLIKAWTH FHFPGRGSTY SDFKWHWYHF DGTDWDESRK LNRIYKFQGK   180
AWDWEVSNEN GNYDYLMYAD IDYDHPDVAA EIKRWGTWYA NELQLDGFRL DAVKHIKFSF   240
LRDWVNHVRE KTGKEMFTVA EYWQNDLGAL ENYLNKTNFN HSVFDVPLHY QFHAASTQGG   300
GYDMRKLLNG TVVSKHPLKS VIFVDNHDTQ PGQSLESTVQ TWFKPLAYAF ILTRESGYPQ   360
VFYGDMYGTK GDSQREIPAL KHKIEPILKA RKQYAYGAQH DYFDHHDIVG WTREGDSSVA   420
NSGLAALITD GPGGAKRMYV GRQNAGETWH DITGNRSEPV VINSEGWGEF HVNGGSVSIY   480
VQR
```

*FIG._4*

Am-Lich = B.llcheniformis   Am-Amylo = B.amyloliquefaciens   Am-Stero = B.stearothermophilus.

```
                                                                                            19
                   1                                                                        60
Am-Lich   ......MKQQ  KRLYARLLTL  LFALIFLLPH  ......SAAA  AANLNGTLMQ  YFEWYMPNDG
Am-Amylo  MRGRGNMIQK  RKRTVSFRLV  LMCTLLFVSL  ......PITK  TSAVNGTLMQ  YFEWYTPNDG
Am-Stearo ......VLTF  HRIIRKGWMF  LLAFLLTASL  FCPTGRHAKA  AAPFNGTMMQ  YFEWYLPDDG 79
          61                                                                               120
Am-Lich   QHWKRLQNDS  AYLAEHGITA  VWIPPAYKGT  SQADVGYGAY  DLYDLGEFHQ  KGTVRTKYGT
Am-Amylo  QHWKRLQNDA  EHLSDIGITA  VWIPPAYKGL  SQSDNGYGPY  DLYDLGEFQQ  KGTVRTKYGT
Am-Stearo TLWTKVANEA  NNLSSLGITA  LSLPPAYKGT  SRSDVGYGVY  DLYDLGEFNQ  KGTVRTKYGT 139
          121                                                                              180
Am-Lich   KGELQSAIKS  LHSRDINVYG  DVVINHKGGA  DATEDVTAVE  VDPADRNRVI  SGEHLIKAWT
Am-Amylo  KSELQDAIGS  LHSRNVQVYG  DVVLNHKAGA  DATEDVTAVE  VNPANRNQET  SEEYQIKAWT
Am-Stearo KAQYLQAIQA  AHAAGMQVYA  DVVFDHKGGA  DGTEWVDAVE  VNPSDRNQEI  SGTYQIQAWT 197
          181                                                                              240
Am-Lich   HFHFPGRGST  YSDFKWHWYH  FDGTDWDESR  KLNRIYKF..  QGKAWDWEVS  NENGNYDYLM
Am-Amylo  DFRFPGRGNT  YSDFKWHWYH  FDGADWDESR  KISRIFKFRG  EGKAWDWEVS  SENGNYDYLM
Am-Stearo KFDFPGRGNT  YSSFKWRWYH  FDGVDWDESR  KLSRIYKFRG  IGKAWDWEVD  TENGNYDYLM 257
          241                                                                              300
Am-Lich   YADIDYDHPD  VAAEIKRWGT  WYANELQLDG  FRLDAVKHIK  FSFLRDWVNH  VREKTGKEMF
Am-Amylo  YADVDYDHPD  VVAETKKWGI  WYANELSLDG  FRIDAAKHIK  FSFLRDWVQA  VRQATGKEMF
Am-Stearo YADLDMDHPE  VVTELKNWGK  WYVNTTNIDG  FRLDGLKHIK  FSFFPDWLSY  VRSQTGKPLF
```

FIG._5A

Am-Lich = B.llcheniformis   Am-Amylo = B.amyloliquefaciens   Am-Stero = B.stearothermophilus.

```
                 301                                                                         317
Am-Lich    TVAEYWQNDL GALENYLNKT NFNHSVFDVP LHYQFHAAST QGGGYDMRKL LNGTVVSKHP
Am-Amylo   TVAEYWQNNA GKLENYLNKT SFNQSVFDVP LHFNLQAASS QGGGYDMRRL LDGTVVSRHP
Am-Stearo  TVGEYWSYDI NKLHNYITKT NGTMSLFDAP LHNKFYTASK SGGAFDMRTL MTNTLMKDQP   360

361                                                                         377
Am-Lich    LKSVTFVDNH DTQPGQSLES TVQTWFKPLA YAFILTRESG YPQVFYGDMY GTKGDSQREI
Am-Amylo   EKAVTFVENH DTQPGQSLES TVQTWFKPLA YAFILTRESG YPQVFYGDMY GTKGTSPKEI
Am-Stearo  TLAVTFVDNH DTNPAKR.CS HGRPWFKPLA YAFILTRQEG YPCVFYGDYY GI...PQYNI   420

421                                                                         437
Am-Lich    PALKHKIEPI LKARKQYAYG AQHDYFDHHD IVGWTREGDS SVANSGLAAL ITDGPGGAKR
Am-Amylo   PSLKDNIEPI LKARKEYAYG PQHDYIDEPD VIGWTREGDS SAAKSGLAAL ITDGPGGSKR
Am-Stearo  PSLKSKIDPL LIARRDYAYG TQHDYLDHSD IIGWTREGVT EKPGSGLAAL ITDGAGRSKW   480

481                                                           483
Am-Lich    MYVGRQNAGE TWHDITGNRS EPVVINSEGW GEFHVNGGSV SIYVQR.....  ........
Am-Amylo   MYAGLKNAGE TWYDITGNRS DTVKIGSDGW GEFHVNDGSV SIYVQK.....  ........
Am-Stearo  MYVGKQHAGK VFYDLTGNRS DTVTINSDGW GEFKVNGGSV SVWVPRKTTV  STIARPITTR   540

541        559
Am-Lich    ..........  ........
Am-Amylo   ..........  ........
Am-Stearo  PWTGEFVRWH  EPRLVAWP*
```

FIG._5B

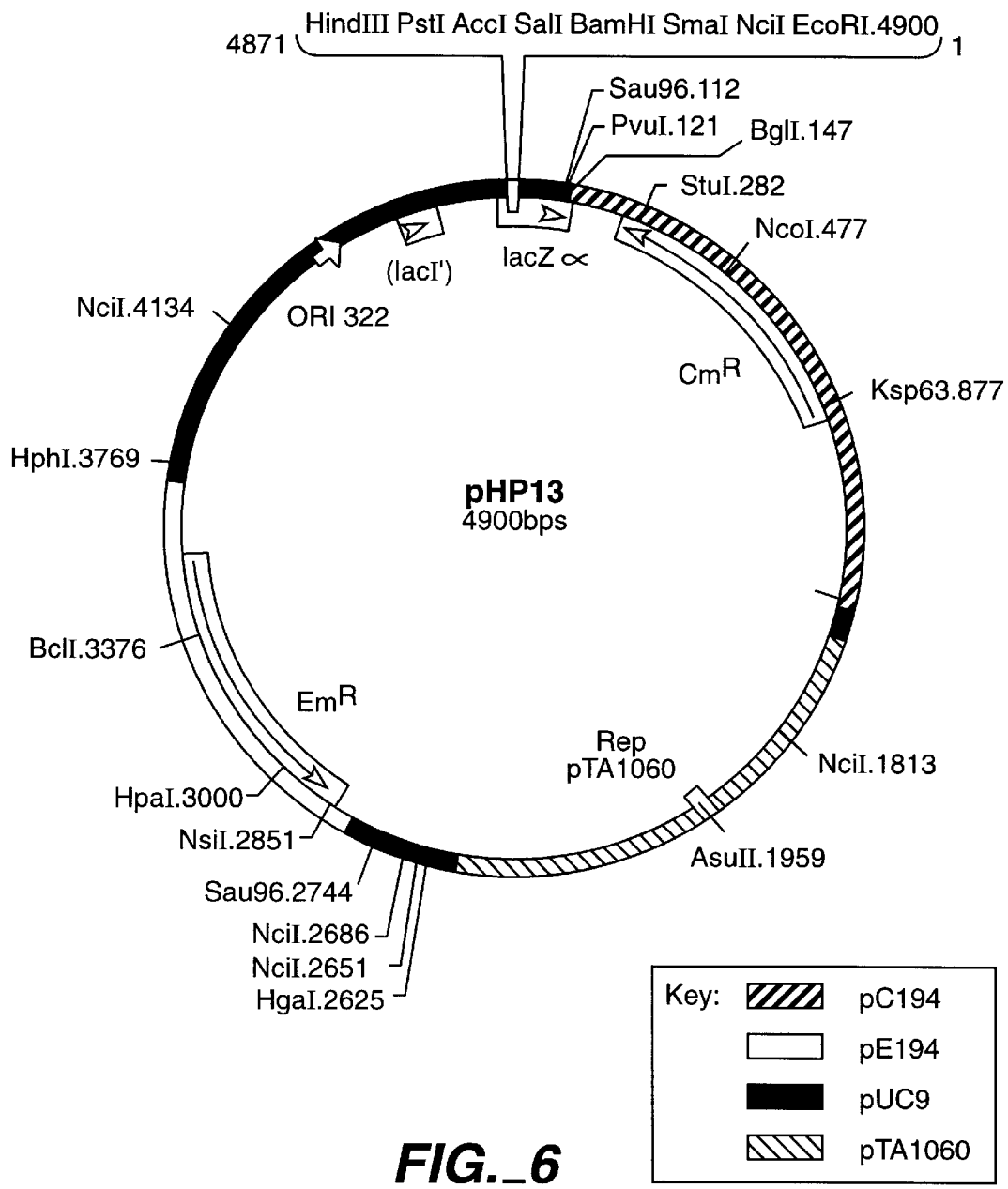
FIG._6

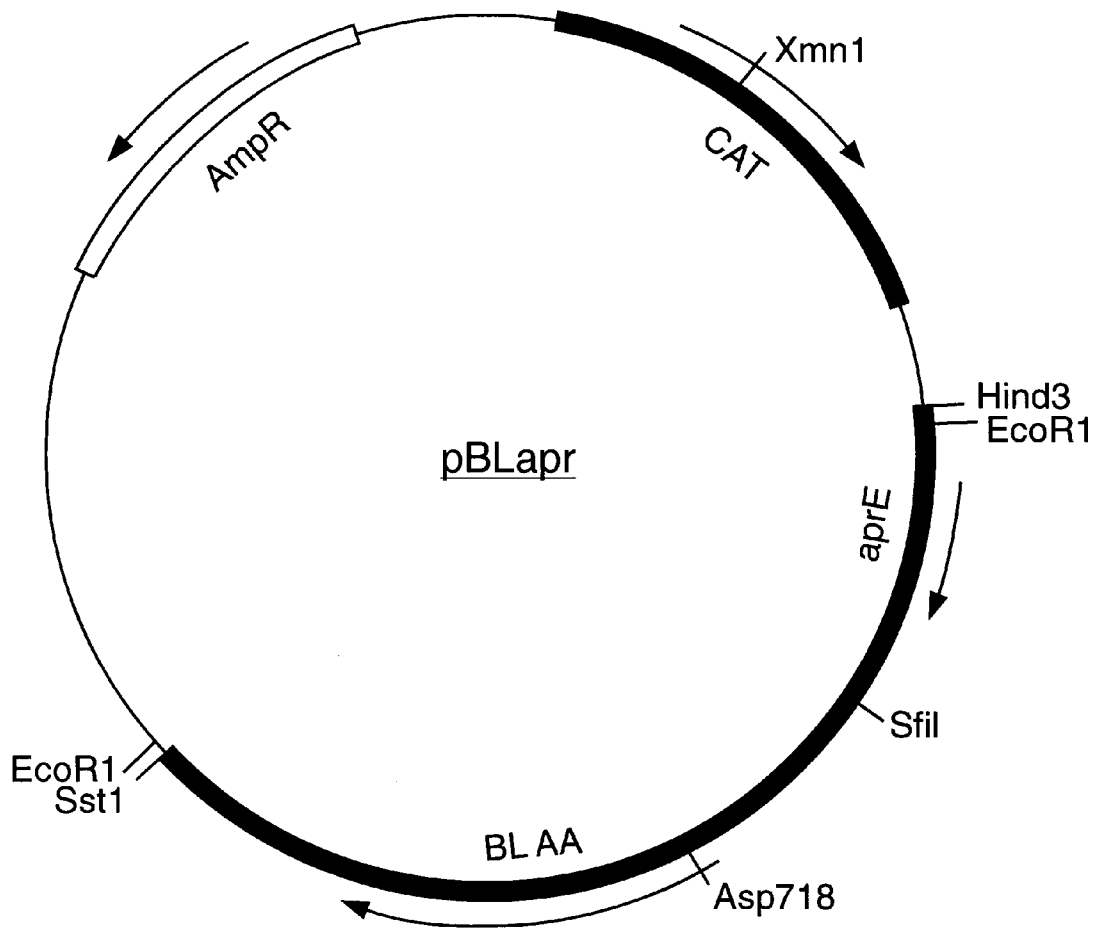
FIG._7

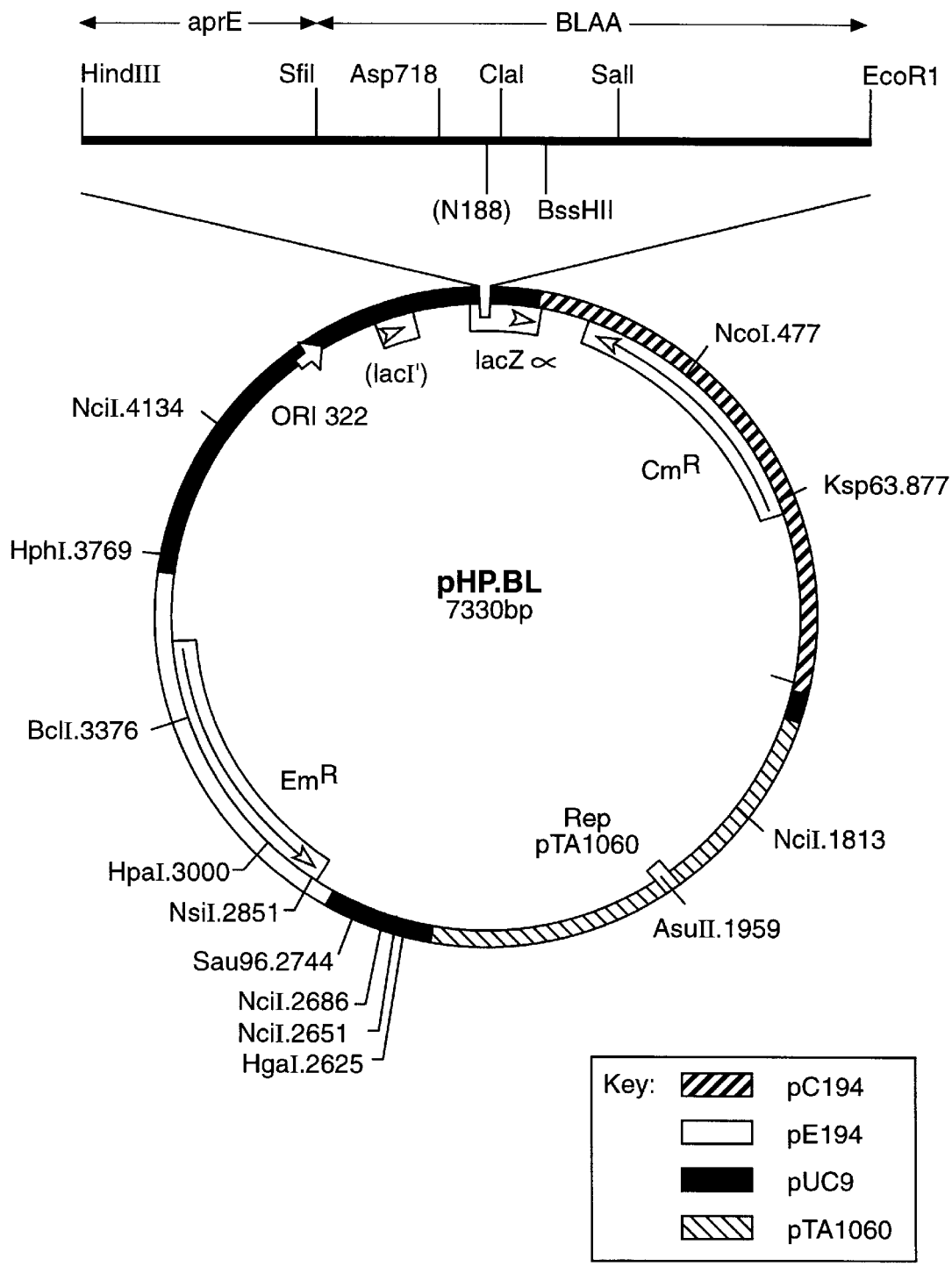
pHP.BL = pHP13 with the 2460bp HindIII-EcoRI insert from pBLapr
*FIG._8*

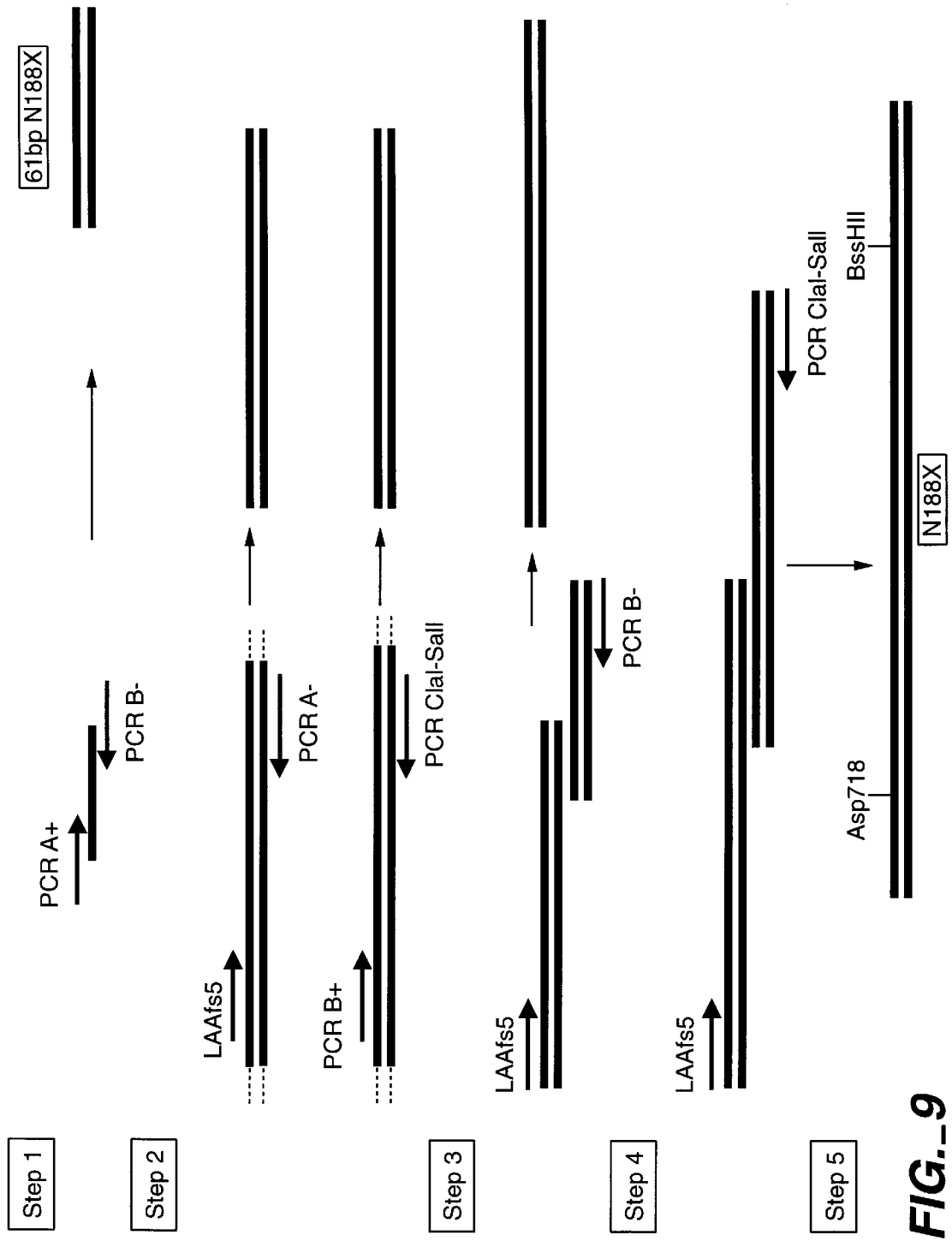
FIG._9

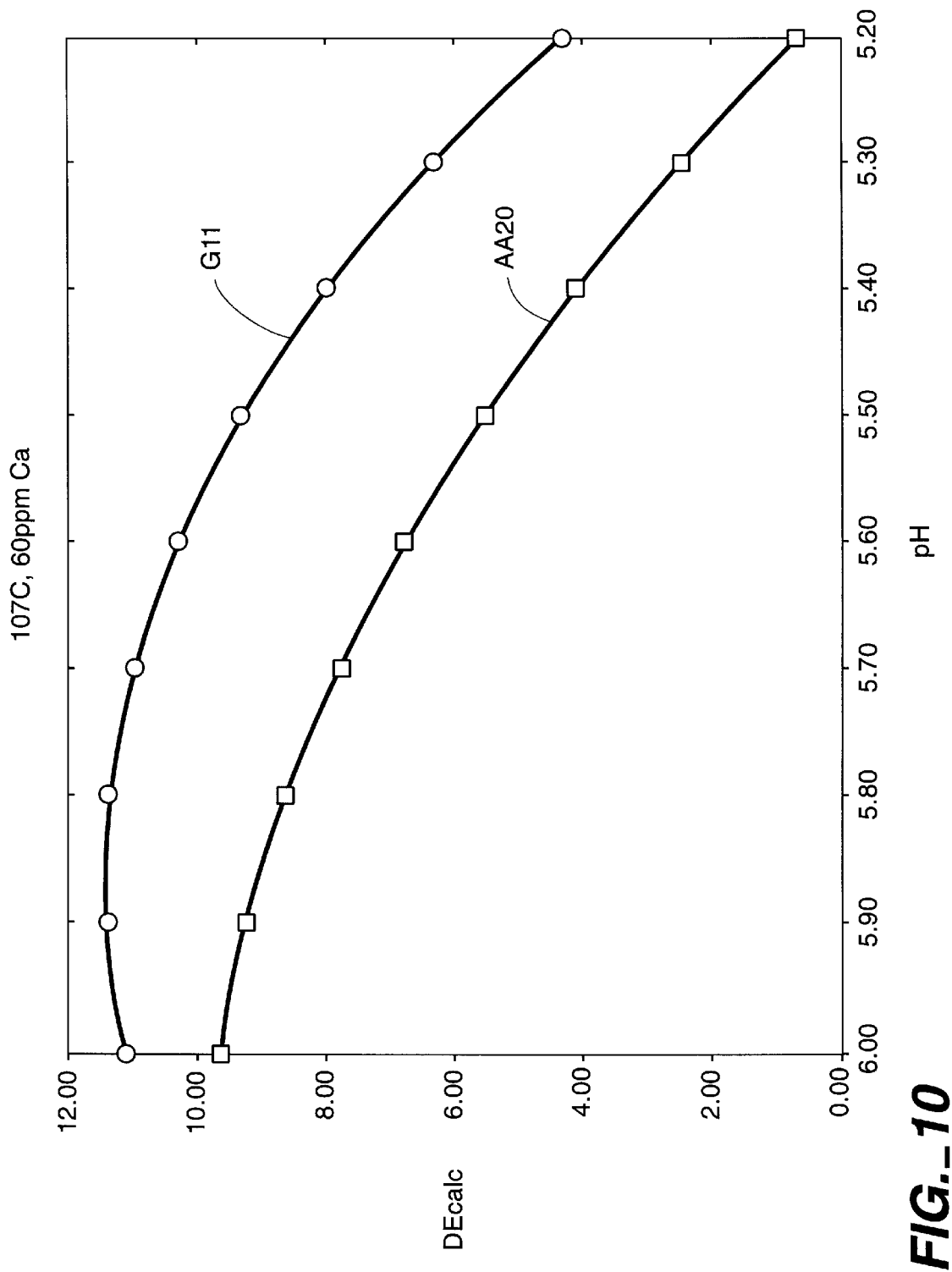
FIG._10

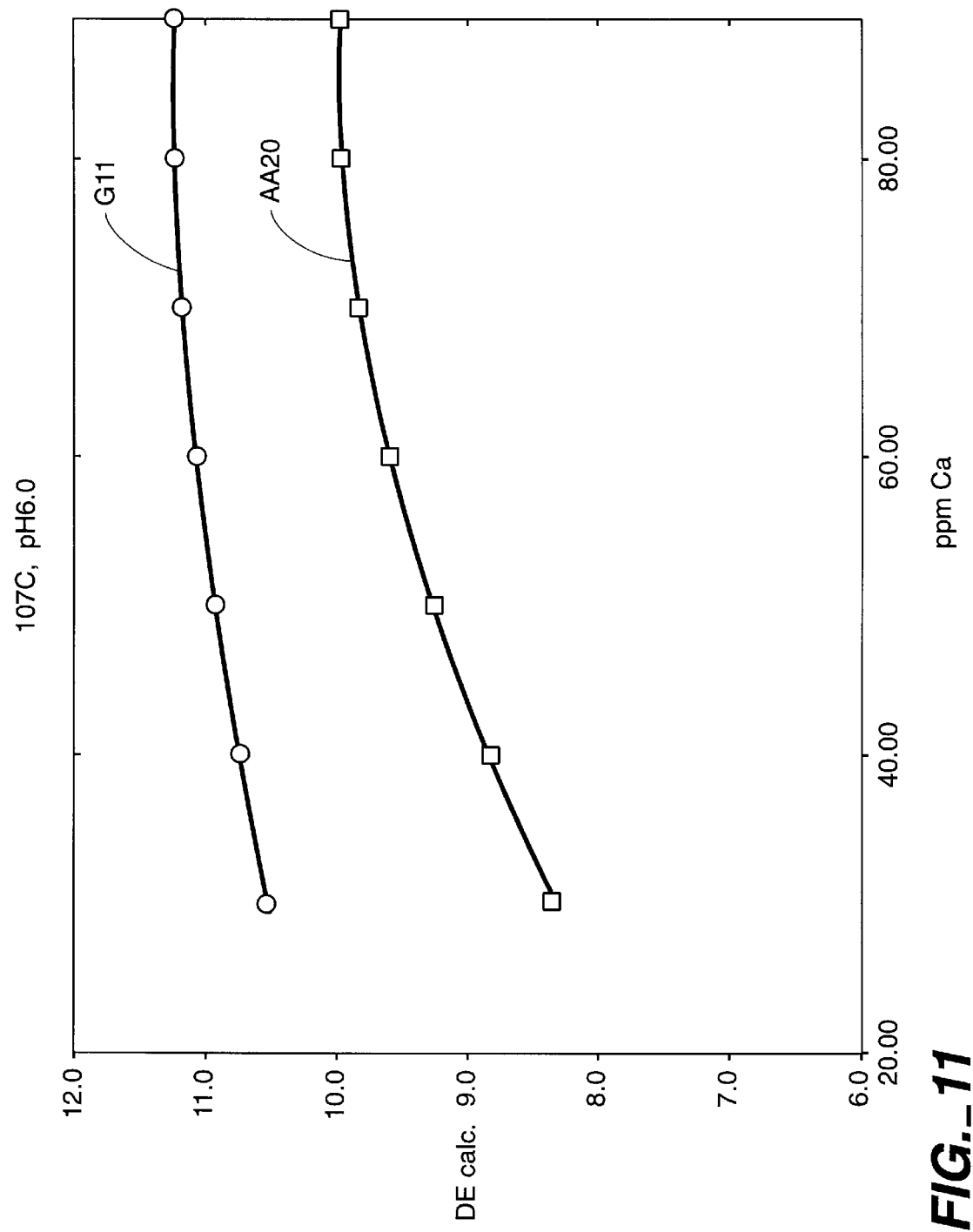
FIG._11

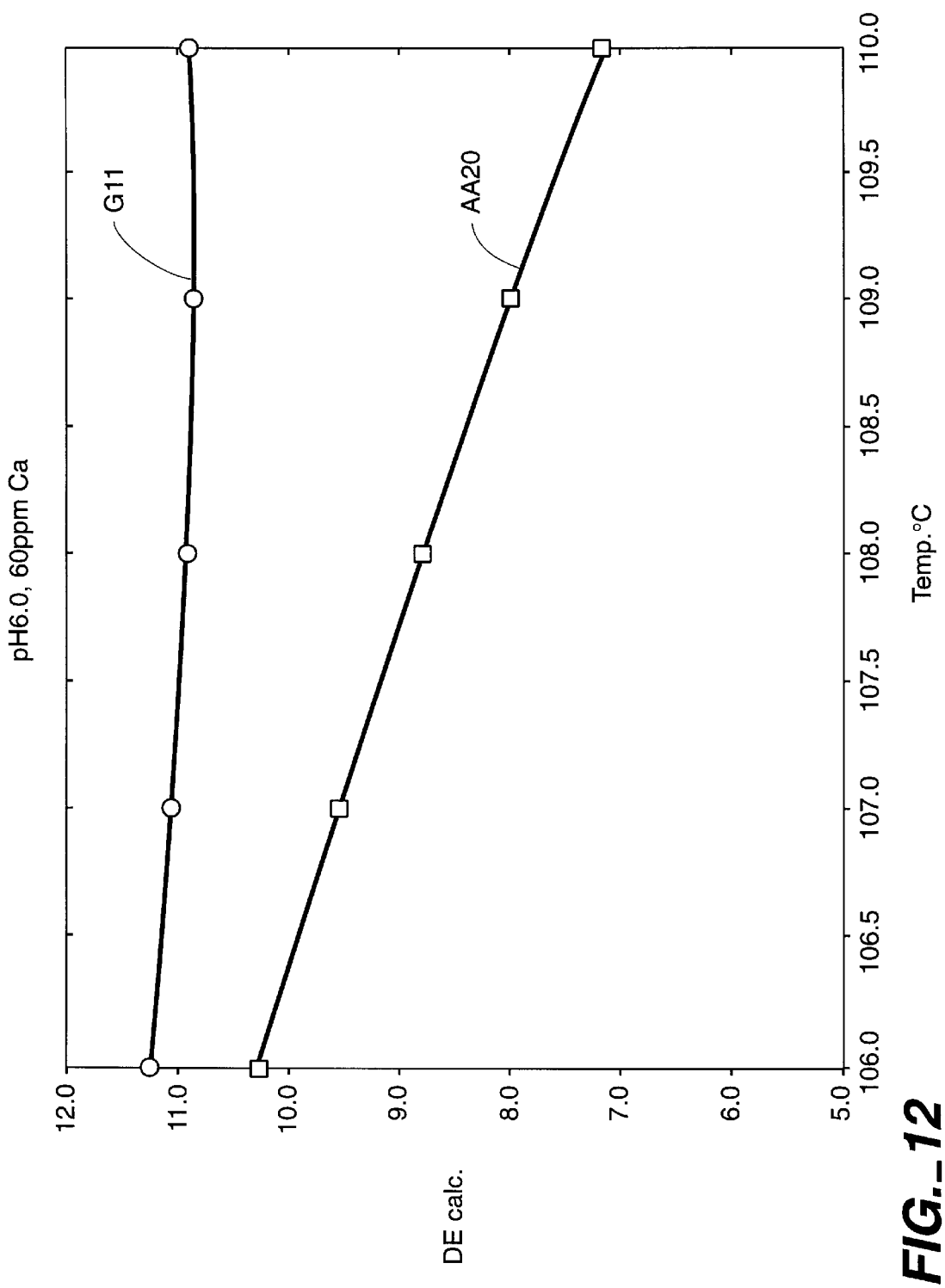
FIG._12

SIGNAL SEQUENCE-MATURE PROTEIN JUNCTIONS IN:

*B.licheniformis*   alpha-amylase.

M K Q Q K R L T A R L L T L L F A L I F L L P H S A A A A A N L . . .
⠀⠀⠀⠀⠀⠀⠀⠀⠀⠀⠀⠀⠀⠀⠀⠀⠀⠀⠀⠀⠀⠀⠀⠀⠀⠀⠀(PstI)↓

*B.subtilis*   alkaline protease aprE.

M R S K T L W I S L L F A L T L I F T M A F S N M S A Q Q A A G K S . . .
⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀(PstI)↓

*B.licheniformis*   alpha-amylase in pBLapr.

M R S K T L W I S L L F A L T L I F T M A F S N M S A Q A A N L . . .

(PstI) →    indicates the site of the restriction site in the gene

BOLD TYPE indicates the N-terminus of the secreted protein in *Bacillus*.

FIG._13

MUTANT α-AMYLASE

FIELD OF THE INVENTION

The present invention is directed to α-amylases having altered performance characteristics. The present invention is also directed to novel mutant α-amylase enzymes having at least an asparagine residue which is substituted with a different amino acid or deleted, wherein the resultant α-amylase exhibits altered low pH starch hydrolysis performance, altered stability and altered activity profiles.

BACKGROUND OF THE INVENTION

α-Amylases (α-1,4-glucan-4-glucanohydrolase, EC 3.2.1.1) hydrolyze internal α-1,4-glucosidic linkages in starch, largely at random, to produce smaller molecular weight malto-dextrins. α-Amylases are of considerable commercial value, being used in the initial stages (liquefaction) of starch processing; in alcohol production; as cleaning agents in detergent matrices; and in the textile industry for starch desizing. α-Amylases are produced by a wide variety of microorganisms including Bacillus and Aspergillus, with most commercial amylases being produced from bacterial sources such as *Bacillus licheniformis*, *Bacillus amyloliquefaciens*, *Bacillus subtilis*, or *Bacillus stearothermophilus*. In recent years, the preferred enzymes in commercial use have been those from *Bacillus licheniformis* because of their heat stability and performance, at least at neutral and mildly alkaline pH's.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from *Bacillus licheniformis*, with the addition of calcium hydroxide, sodium hydroxide or sodium carbonate. The addition of calcium hydroxide has the advantage of also providing calcium ions which are known to stabilize the α-amylases against inactivation. Upon addition of α-amylases, the suspension is pumped through a steam jet to instantaneously raise the temperature to between 80–115° C. The starch is immediately gelatinized and, due to the presence of α-amylases, depolymerized through random hydrolysis of α(1–4) glycosidic bonds to a fluid mass which is easily pumped.

In a second variation to the liquefaction process, α-amylase is added to the starch suspension, the suspension is held at a temperature of 80–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was obtained and the molecular structure of the α-amylase molecule. α-Amylases produced by wild type strains of *Bacillus subtilis* or *Bacillus amyloliquefaciens* are typically used at temperatures no greater than about 90° C. due to excessively rapid thermal inactivation above that temperature, whereas α-amylases produced by wild type strains of *Bacillus licheniformis* can be used at temperatures up to about 110° C. The presence of starch and calcium ion are known to stabilize α-amylases against inactivation. Nonetheless, α-amylases are used at pH values above 6 to protect against rapid inactivation. At low temperatures, α-amylase from *Bacillus licheniformis* is known to display hydrolyzing activity on starch substrate at pH values as low as 5. However, when the enzyme is used for starch hydrolysis at common jet temperatures, e.g., between 102° C. and 109° C., the pH must be maintained above at least pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH is generally maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose with glucoamylase, requires a pH of 4–4.5; therefore, the pH must be adjusted down from 5.9–6.0 to 4–4.5; requiring additional chemical addition and refining steps.

Subsequent to liquefaction, the processed starch is saccharified to glucose with glucoamylase. A problem with present processes occurs when residual starch is present in the saccharification mixture due to an incomplete liquefaction of the starch, e.g., inefficient amylose hydrolysis by amylase. Residual starch is highly resistant to glucoamylase hydrolysis. It represents a yield loss and interferes with downstream filtration of the syrups.

Additionally, many α-amylases are known to require the addition of calcium ion for stability. This further increases the cost of liquefaction.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or α-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 94/02597, a mutant α-amylase having improved oxidative stability is described wherein one or more methionines are replaced by any amino acid except cysteine or methionine.

In PCT publication No. WO 94/18314, a mutant α-amylase having improved oxidative stability is described wherein one or more of the methionine, tryptophan, cysteine, histidine or tyrosine residues is replaced with a non-oxidizable amino acid.

In PCT Publication No. WO 91/00353, the performance characteristics and problems associated with liquefaction with wild type *Bacillus licheniformis* α-amylase are approached by genetically engineering the α-amylase to include the specific substitutions Ala-111-Thr, His-133-Tyr and/or Thr-149-Ile.

Studies using recombinant DNA techniques to explore which residues are important for the catalytic activity of amylases and/or to explore the effect of modifying certain amino acids within the active site of various amylases and glycosylases have been conducted by various researchers (Vihinen et al., J. Biochem., vol. 107, pp. 267–272 (1990); Holm et al., Protein Engineering, vol. 3, pp. 181–191 (1990); Takase et al., Biochemica et Biophysica Acta, vol. 1120, pp. 281–288 (1992); Matsui et al., Febs Letters, vol. 310, pp. 216–218 (1992); Matsui et al., Biochemistry, vol. 33, pp. 451–458 (1992); Sogaard et al., J. Biol. Chem., vol. 268, pp. 22480–22484 (1993); Sogaard et al., Carbohydrate Polymers, vol. 21, pp. 137–146 (1993); Svensson, Plant Mol. Biol., vol. 25, pp. 141–157 (1994); Svensson et al., J. Biotech. vol. 29, pp. 1–37 (1993)). Researchers have also studied which residues are important for thermal stability (Suzuki et al., J. Biol. Chem. vol. 264, pp. 18933–18938 (1989); Watanabe et al., Eur. J. Biochem. vol. 226, pp. 277–283 (1994)); and one group has used such methods to introduce mutations at various histidine residues in a *Bacillus licheniformis* amylase, the rationale being that *Bacillus licheniformis* amylase which is known to be relatively thermostable when compared to other similar Bacillus amylases, has an excess of histidines and, therefore, it was suggested that replacing a histidine could affect the thermostability of the enzyme. This work resulted in the identification of stabilizing mutations at the histidine residue at the +133 position and the alanine residue at position +209 (Declerck et al., J. Biol. Chem., vol. 265, pp. 15481–15488 (1990); FR 2 665 178-A1; Joyet et al., Bio/Technology, vol. 10, pp. 1579–1583 (1992)).

Despite the advances made in the prior art, a need exists for an α-amylase which is effective enough at low pH values to allow commercial liquefaction at lower pH than currently practical. Similarly, a need exists in the art for a method which allows efficient liquefaction of dry milled grain at high temperatures. Further, a need exists in the art for a method which allows the efficient liquefaction of starch with a decreased reliance on the costly addition of calcium. Additionally, a need exists for a more efficient enzyme to effect a more complete hydrolysis of starch at the liquefaction stage to ensure efficient saccharification. Because commercially available amylases are not acceptable under many conditions due to stability problems, for example, the high alkalinity and oxidant (bleach) levels associated with detergents, there is a need for an amylase having altered, and preferably increased, performance profiles under such conditions. Thus, altered performance characteristics such as increased activity, thermostability, pH stability, oxidative stability or calcium stability which can be achieved while also altering, maintaining, or increasing enzymatic activity as compared to the wild type or precursor enzyme, would be desirable.

SUMMARY OF THE INVENTION

It is an object of the present invention to provide an α-amylase having altered performance profiles, such as pH stability, alkaline stability, oxidative stability or enzymatic activity.

It is a further object of the present invention to provide an α-amylase having increased stability in the absence of added calcium ion during liquefaction of starch.

It is a further object of the present invention to provide an α-amylase having altered low pH stability for use in efficient low pH liquefaction.

It is yet a further object of the present invention to provide an α-amylase which allows efficient liquefaction of dry milled grain at high temperatures.

It is still a further object of the present invention to provide an α-amylase which is useful in high pH environments or in the presence of oxidants or bleach.

It is still a further object of the present invention to provide an α-amylase which effects a more complete hydrolysis of starch molecules to increase the efficiency of saccharification.

According to the present invention, an α-amylase is provided that is the expression product of a mutated DNA sequence encoding an α-amylase, the mutated DNA sequence being derived from a precursor α-amylase by the deletion or substitution of one or more residues having the effect to improve the performance of the α-amylase residues.

Preferably, the deleted or substituted residue is an asparagine residue, most preferably at a position corresponding to N188 in *Bacillus licheniformis*. Where it is desired to alter the thermostability of the α-amylase, the asparagine substitution may be any other amino acid, including any of the 20 naturally occurring amino acids. Preferably, the substitution corresponds to N188S or N188T in *Bacillus licheniformis*. Also preferably, the α-amylase further comprises the deletion or substitution of a methionine or tryptophan residue, particularly at a position corresponding to M15, W138 and/or M197, or at a residue corresponding to V128, H133, S187 and/or A209 in *Bacillus licheniformis*. In a most preferred embodiment, an α-amylase is provided comprising substitutions at residues corresponding to M15L/N188S or M15T/N188S in *Bacillus licheniformis*.

BRIEF DESCRIPTION OF THE DRAWINGS

FIG. 1 illustrates mutagenic oligonucleotides useful during directed mutagenesis of Ans188 from *Bacillus licheni-* formis α-amylase. In this and following figures illustrating oligonucleotide constructs, bold letters indicate base changes introduced by the oligonucleotide and underlining indicates restriction endonuclease sites introduced by the oligonucleotide.

FIG. 2 illustrates PCR primers used for PCR processing of mutagenic oligonucleotide templates.

FIG. 3 illustrates the DNA sequence of the gene for α-amylase from *Bacillus licheniformis* (NCIB 8061) (SEQ ID NO:33) and deduced amino acid sequence of the translation product (SEQ ID NO:41) as described by Gray et al., J. Bacteriology, vol. 166, pp. 635–643 (1986).

FIG. 4 illustrates the amino acid sequence (SEQ ID NO:34) of the mature α-amylase enzyme from *Bacillus licheniformis*.

FIG. 5 illustrates an alignment of the primary structures of three Bacillus α-amylases. The *Bacillus licheniformis* α-amylase (Am-Lich) (SEQ ID NO:35) is described by Gray et al., J. Bacteriology, vol. 166, pp. 635–643 (1986); the *Bacillus amyloliquefaciens* α-amylase (Am-Amylo) (SEQ ID NO:36) is described by Takkinen et al., J. Biol. Chem., vol. 258, pp. 1007–1013 (1983); and the *Bacillus stearothermophilus* α-amylase (Am-Stearo) (SEQ ID NO:37) is described by Ihara et al., J. Biochem., vol. 98, pp. 95–103 (1985).

FIG. 6 illustrates plasmid pHP13 wherein $Cm^R$ refers to chloramphenicol resistance, $Em^R$ refers to erythromycin resistance and Rep pTA1060 refers to the origin of replication from plasmid pTA1060.

FIG. 7 illustrates the pBLapr plasmid wherein BL AA refers to *Bacillus licheniformis* α-amylase gene; aprE refers to the promoter and signal peptide encoding region of the aprE gene; AmpR refers to the ampicillin resistant gene from pBR322; and CAT refers to the chloramphenicol resistance gene from pC194.

FIG. 8 illustrates the pHP.BL plasmid carrying the gene for *Bacillus licheniformis* α-amylase.

FIG. 9 illustrates a schematic of the PCR method used to produce the mutant oligonucleotides corresponding to α-amylase derived from *Bacillus licheniformis*.

FIG. 10 illustrates a graph derived from a statistical analysis of variant enzyme according to the invention, M15T/N188S, compared to wild type *Bacillus licheniformis* α-amylase in starch liquefaction at 107° C., 60 ppm calcium and varying pH.

FIG. 11 illustrates a graph derived from a statistical analysis of the performance of a variant enzyme according to the invention, M15T/N188S, compared to wild type *Bacillus licheniformis* α-amylase in starch liquefaction at 107° C., pH 6.0 and varying calcium concentration.

FIG. 12 illustrates a graph derived from a statistical analysis of the performance of a variant enzyme according to the invention, M15T/N188S, compared to wild type *Bacillus licheniformis* α-amylase in starch liquefaction at pH 6.0, 60 ppm calcium and varying temperature.

FIG. 13 illustrates the signal sequence-mature protein junctions in α-amylase derived from *Bacillus licheniformis* (SEQ ID NO:38), *Bacillus subtilis* aprE (SEQ ID NO:39) and *Bacillus licheniformis* in pBLapr (SEQ ID NO:40).

DETAILED DESCRIPTION

"α-Amylase" means an enzymatic activity which cleaves or hydrolyzes the α(1-4)glycosidic bond, e.g., that in starch, amylopectin or amylose polymers. α-Amylase as used herein includes naturally occurring α-amylases as well as recombinant α-amylases. Preferred α-amylases in the present invention are those derived from *Bacillus licheniformis, Bacillus amyloliquefaciens* or *Bacillus stearothermophilus,* as well as fungal α-amylases such as those derived from Aspergillus (i.e., *A. oryzae* and *A. niger*.

"Recombinant α-amylase" means an α-amylase in which the DNA sequence encoding the naturally occurring α-amylase is modified to produce a mutant DNA sequence which encodes the substitution, insertion or deletion of one or more amino acids in the α-amylase sequence compared to the naturally occurring α-amylase.

"Expression vector" means a DNA construct comprising a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *Bacillus subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

"Host strain" or "host cell" means a suitable host for an expression vector comprising DNA encoding the α-amylase according to the present invention. Host cells useful in the present invention are generally procaryotic or eucaryotic hosts, including any transformable microorganism in which the expression of α-amylase according to the present invention can be achieved. Specifically, host strains of the same species or genus from which the α-amylase is derived are suitable, such as a Bacillus strain. Preferably, an α-amylase negative Bacillus strain (genes deleted) and/or an α-amylase and protease deleted Bacillus strain (ΔamyE, Δapr, Δnpr) is used. Host cells are transformed or transfected with vectors constructed using recombinant DNA techniques. Such transformed host cells are capable of either replicating vectors encoding the α-amylase and its variants (mutants) or expressing the desired α-amylase.

"Liquefaction" or "liquefy" means a process by which starch is converted to shorter chain and less viscous dextrins. Generally, this process involves gelatinization of starch simultaneously with or followed by the addition of α-amylase.

According to the present invention, an α-amylase is provided that is the expression product of a mutated DNA sequence encoding an α-amylase, the mutated DNA sequence being derived from a precursor α-amylase by the deletion or substitution of one or more asparagine residues. Also provided is a nucleic acid molecule (DNA) which encodes an amino acid sequence comprising at least a part of the α-amylase provided by the present invention, expression systems incorporating such DNA including vectors and phages, host cells transformed with such DNA, and antisense strands of DNA corresponding to the DNA molecule which encodes the amino acid sequence. Similarly, the present invention includes a method for producing an α-amylase by expressing the DNA incorporated on an expression system which has been transformed into a host cell. The α-amylase of the invention may be used in liquefaction of starch, as an ingredient in detergents, in food processing, in textile processing, or in any other application in which α-amylase activity is useful.

The α-amylases according to the present invention comprise an amino acid sequence which is derived from the amino acid sequence of a precursor α-amylase. The precursor α-amylases include naturally occurring α-amylases and recombinant α-amylases. The amino acid sequence of the α-amylase mutant is derived from the precursor α-amylase amino acid sequence by the substitution, deletion or insertion of one or more amino acids of the precursor amino acid sequence. Such modification is generally of the precursor DNA sequence which encodes the amino acid sequence of the precursor α-amylase rather than manipulation of the precursor α-amylase enzyme per se. Suitable methods for such manipulation of the precursor DNA sequence include methods disclosed herein and in commonly owned U.S. Pat. Nos. 4,760,025 and 5,185,258, incorporated herein by reference.

The α-amylases according to the present invention are derived from a precursor amylase. The precursor α-amylase is produced by any source capable of producing α-amylase. Suitable sources of α-amylases are prokaryotic or eukaryotic organisms, including fungi, bacteria, plants or animals. Preferably, the precursor α-amylase is produced by a Bacillus; more preferably, by *Bacillus licheniformis, Bacillus amyloliquefaciens* or *Bacillus stearothermophilus*; most preferably, the precursor α-amylase is derived from *Bacillus licheniformis*.

Homologies have been found between almost all endo-amylases sequenced to date, ranging from plants, mammals, and bacteria (Nakajima et al., Appl. Microbiol. Biotechnol., vol. 23, pp. 355–360 (1986); Rogers, Biochem. Biophys. Res. Commun., vol. 128, pp. 470–476 (1985); Janecek, Eur. J. Biochem., vol. 224, pp. 519–524 (1994)). There are four areas of particularly high homology in certain Bacillus amylases, as shown in FIG. 5, wherein the underlined sections designate the areas of high homology. Sequence alignments have also been used to map the relationship between Bacillus endo-amylases (Feng et al., J. Molec. Evol., vol. 35, pp. 351–360 (1987)). The relative sequence homology between *Bacillus stearothermophilus* and *Bacillus licheniformis* amylase is about 66% and that between *Bacillus licheniformis* and *Bacillus amyloliquefaciens* amylases is about 81%, as determined by Holm et al., Protein Engineering, vol. 3, No. 3, pp. 181–191 (1990). While sequence homology is important, it is generally recognized that structural homology is also important in comparing amylases or other enzymes. For example, structural homology between fungal amylases and bacterial amylase has been suggested and, therefore, fungal amylases are encompassed within the present invention.

Among others, residues corresponding to asparagine residues in α-amylase are identified herein for deletion or substitution. Thus, specific residues such as N188 refer to an amino acid position number (i.e., +188) which references the number assigned to the mature *Bacillus licheniformis* α-amylase sequence illustrated in FIG. 4. The invention, however, is not limited to the mutation of the particular mature α-amylase of *Bacillus licheniformis* but extends to precursor α-amylases containing amino acid residues at positions which are equivalent to the particular identified residue in *Bacillus licheniformis* α-amylase. A residue of a precursor α-amylase is equivalent to a residue of *Bacillus licheniformis* α-amylase if it is either homologous (i.e., corresponds in position for either the primary or tertiary structure) or analogous to a specific residue or portion of that residue in *Bacillus licheniformis* α-amylase (i.e., having the same or similar functional capacity to combine, react, or interact chemically or structurally).

In order to establish homology to primary structure, the amino acid sequence of a precursor α-amylase is directly compared to the *Bacillus licheniformis* α-amylase primary sequence and particularly to a set of residues known to be invariant to all α-amylases for which sequences are known (see e.g., FIG. 7). It is possible also to determine equivalent residues by tertiary structure analysis of the crystal structures reported for porcine pancreatic α-amylase (Buisson et al., EMBO Journal, vol. 6, pp. 3909–3916 (1987); Qian et al., Biochemistry, vol. 33, pp. 6284–6294 (1994); Larson et al., J. Mol. Biol., vol. 235, pp. 1560–1584 (1994)); Taka-amylase A from *Aspergillus oryzae* (Matsuura et al., J. Biochem. (Tokyo), vol. 95, pp. 697–702 (1984)); and an acid α-amylase from *A. niger* (Boel et al. Biochemistry, vol. 29, pp. 6244–6249 (1990)), with the former two structures being similar, and for barley α-amylase (Vallee et al., J. Mol. Biol., vol. 236, pp. 368–371(1994); Kadziola, J. Mol. Biol., vol. 239, pp.104–121 (1994)). Although there have been some preliminary studies published (Suzuki et al, J. Biochem., vol. 108, pp. 379–381 (1990); Lee et al., Arch. Biochem. Biophys, vol. 291, pp. 255–257 (1991); Chang et al, J. Mol. Biol., vol. 229, pp. 235–238 (1993); Mizuno et al., J. Mol. Biol., vol. 234, pp. 1282–1283 (1993)), there is only a published structure for *Bacillus licheniformis* α-amylase (Machius et al., J. Mol. Biol. vol. 246, pp. 545–549 (1995)). However, several researchers have predicted common super-secondary structures between glucanases (MacGregor et al., Biochem. J., vol. 259, pp. 145–152 (1989)) and within α-amylases and other starch-metabolising enzymes (Jaspersen, J. Prot. Chem. vol. 12, pp. 791–805 (1993); MacGregor, Starke, vol. 45, pp. 232–237 (1993)); and sequence similarities between enzymes with similar super-secondary structures to α-amylases (Janecek, FEBS Letters, vol. 316, pp. 23–26 (1993); Janecek et al., J. Prot. Chem., vol. 12, pp. 509–514 (1993)). A structure for the *Bacillus stearothermophilus* enzyme has been modeled on that of Taka-amylase A (Holm et al., Protein Engineering, vol. 3, pp. 181–191 (1990)). The four highly conserved regions shown in FIG. 7 contain many residues thought to be part of the active-site (Matsuura et al., J. Biochem. (Tokyo), vol. 95, pp. 697–702 (1984); Buisson et al., EMBO Journal, vol. 6, pp. 3909–3916 (1987); Vihinen et al., J. Biochem., vol. 107, pp. 267–272 (1990)) including His+105; Arg+229; Asp+231; His+235; Glu+261 and Asp+328 under the *Bacillus licheniformis* numbering system.

Preferably, the deleted or substituted asparagine residue is at a position corresponding to N188 in *Bacillus licheniformis*. Where it is desired to alter the thermostability of the α-amylase, the asparagine substitution may be any other amino acid, including any of the 20 naturally occurring amino acids. Preferably, the deletion or substitution corresponds to N188S or N188T in *Bacillus licheniformis*. Also preferably, the α-amylase further comprises the deletion or substitution of a methionine or tryptophan residue.

The α-amylases according to the present invention exhibit altered performance characteristics providing desirable and unexpected results which are useful in the various applications for which α-amylases are commonly used. For example, α-amylases according to the present invention which exhibit altered performance characteristics at low pH, including improved thermostability, improved pH stability and/or improved oxidative stability, are useful in low pH liquefaction of starch. Enhanced thermostability will be useful in extending the shelf life of products which incorporate them. Enhanced oxidative stability or improved performance is particularly desirable in cleaning products, and for extending the shelf life of α-amylase in the presence of bleach, perborate, percarbonate or peracids used in such cleaning products. To the contrary, reduced thermal stability or oxidative stability may be useful in industrial processes which require the rapid and efficient quenching of amylolytic activity.

The α-amylase of the present invention is especially useful in starch processing and particularly in starch liquefaction. Conditions present during commercially desirable liquefaction processes characteristically include low pH, high temperature and potential oxidation conditions requiring α-amylases exhibiting improved low pH performance, improved thermal stability and improved oxidative stability. Accordingly, α-amylases according to the present invention which are particularly useful in liquefaction exhibit improved performance at a pH of less than about 6, preferably less than about 5.5, and most preferably between about 5.0 and 5.5. Additionally, α-amylases according to the present invention which exhibit increased thermal stability at temperatures of between about 80–120° C., and preferably between about 100–110° C., and increased stability in the presence of oxidants will be particularly useful. Preferably, the α-amylase according to the present invention which is used in liquefaction, in addition to deletion or substitution of an asparagine, further comprises a deletion or substitution at one or more residues corresponding to M15, V128, H133, W138, S187, M197 and/or A209 in *Bacillus licheniformis*. In a more preferred embodiment, α-amylase used in starch liquefaction according to the present invention comprises a deletion or substitution corresponding to position N188. Most preferably, the amylase comprises a substitution corresponding to M15T/N188S, M15L/N188S, M15T/H133Y/N188S, M15T/H133Y/N188S/A209V, M15T/N188S/A209V, M15T/V128E/H133Y/N188S, M15T/S187D/N188S, M15T/H13 or M15T/H 133Y/A209V in *Bacillus licheniformis*.

Additional components known by those skilled in the art to be useful in liquefaction, including, for example, antioxidants, calcium, ions, salts or other enzymes such as endoglycosidases, cellulases, proteases, lipases or other amylase enzymes may be added depending on the intended reaction conditions. For example, combinations of the α-amylase according to the present invention with α-amylases from other sources may provide unique action profiles which find particular use under specific liquefaction conditions. In particular, it is contemplated that the combination of the α-amylase according to the present invention with α-amylase derived from *Bacillus stearothermophilus* will provide enhanced liquefaction at pH values below 5.5 due to complementary action patterns. A preferred embodiment where the process involves the liquefaction of dry milled starch for ethanol production comprises α-amylase derived from *Bacillus stearothermophilus* and α-amylase according to the present invention having a substitution corresponding to M15T/N188S or M15L/N188S in *Bacillus licheniformis*.

During liquefaction, starch, specifically granular starch slurries from either a wet or dry milled process, is treated with an α-amylase of the present invention according to known liquefaction techniques. Generally, in the first step of the starch degradation process, the starch slurry is gelatinized by heating at a relatively high temperature (between about 80° C. and about 110° C.). After the starch slurry is gelatinized, it is liquefied using an α-amylase.

In another embodiment of the present invention there are provided detergent compositions in either liquid, gel or granular form, which comprise the α-amylase according to the present invention. Such detergent compositions will particularly benefit from the addition of an α-amylase according to the present invention which has increased thermal stability to improve shelf-life or increased oxidative stability such that the α-amylase has improved resistance to bleach or peracid compounds commonly present in detergents. Thus, α-amylase according to the present invention may be advantageously formulated into known powdered, liquid or gel detergents having a pH of between about 6.5 and about 12.0. A preferred embodiment of the present invention further comprises the deletion or substitution of a methionine residue or a tryptophan residue, for example M15, M197 or W138 as described in commonly assigned U.S. patent application Ser. Nos. 08/289,351 and 08/409,771, the disclosures of which are incorporated by reference; substitution at M133Y as described in PCT Publication No. WO 91/00353; or substitution at A209 as described in DeClerck, et al., J. Biol. Chem., vol. 265, pp. 15481–15488 (1990). Also preferably, an α-amylase according to the present invention used in detergent compositions comprises a deletion or substitution at position N188. Detergent compositions comprising the α-amylase according to the present invention may further include other enzymes such as endoglycosidases, cellulases, proteases, lipases or other amylase enzymes, particularly α-amylase derived from *Bacillus stearothermophilus*, as well as additional ingredients as generally known in the art.

Embodiments of the present invention which comprise a combination of the α-amylase according to the present invention with protease enzymes preferably include oxidatively stable proteases such as those described in U.S. Re. Pat. No. 34,606, incorporated herein by reference, as well as commercially available enzymes such as DURAZYM (Novo Nordisk), MAXAPEM (Gist-brocades) and PURAFECT® OxP (Genencor International, Inc.). Methods for making such protease mutants (oxidatively stable proteases), and particularly such mutants having a substitution for the methionine at a position equivalent to M222 in *Bacillus amyloliquefaciens*, are described in U.S. Re. Pat. No. 34,606.

An additional embodiment of the present invention comprises DNA encoding an α-amylase according to the present invention and expression vectors comprising such DNA. The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose. In addition, any of a wide variety of expression control sequences are generally used in these vectors. For example, Applicants have discovered that a preferred expression control sequence for Bacillus transformants is the aprE signal peptide derived from *Bacillus subtilis*.

A wide variety of host cells are also useful in expressing the DNA sequences of this invention. These hosts may include well known eukaryotic and prokaryotic hosts, such as strains of *E. coli,* Pseudomonas, Bacillus, Streptomyces, various fungi, yeast and animal cells. Preferably, the host expresses the α-amylase of the present invention extracellularly to facilitate purification and downstream processing. Expression and purification of the mutant α-amylase of the invention may be effected through art-recognized means for carrying out such processes.

The improved α-amylases according to the present invention provide several important advantages when compared to wild type Bacillus α-amylases. For example, one advantage is the increased activity found at low pH and high temperatures typical of common starch liquefaction methods. Another advantage is the increased high pH and oxidative stability which facilitates their use in detergents. Another advantage is that a more complete hydrolysis of starch molecules is achieved which reduces residual starch in the processing stream. Yet another advantage is their improved stability in the absence of calcium ion. Yet another advantage is that the addition of equal protein doses of α-amylase according to the invention provide superior performance when compared to wild type *Bacillus licheniformis* α-amylase due to improvements in both specific activity and stability under stressed conditions. In other words, because of the generally increased stability of the amylases according to the present invention, the increased specific activity on starch of the inventive amylases translates to even greater potential performance benefits of this variant. Under conditions where the wild type enzyme is being inactivated, not only does more of the inventive amylase survive because of its increased stability, but also that which does survive expresses proportionally more activity because of its increased specific activity.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

EXAMPLES

Example 1

Construction of Plasmid pHP.BL

The α-amylase gene shown in FIG. 3 was cloned from *Bacillus licheniformis* NCIB8061 (Gray et al., J. Bacteriology, vol. 166, pp. 635–643 (1986)). The 1.72 kb PstI-SstI fragment, encoding the last three residues of the signal sequence, the entire mature protein and the terminator region, was subcloned into M13mp18. A synthetic terminator was added between the BclI and SstI sites using a synthetic oligonucleotide cassette of the form:

```
BclI                                                         SstI
5'-GATCAAAACATAAAAAACCGGCCTTGGCCCCGCCGGTTTTTATTATTTTTGAGCT-3' (SEQ ID NO:1)

3'     TTTTGTATTTTTTGGCCGGAACCGGGGCGGCCAAAAAATAATAAAAAC    5' (SEQ ID NO:2)
``` designed to contain the *Bacillus amyloliquefaciens* subtilisin transcriptional terminator (Wells et al., Nucleic Acid Research, vol. 11, pp. 7911–7925 (1983)).

The pBLapr plasmid was constructed carrying the gene for the *Bacillus licheniformis* α-amylase. As illustrated in FIG. 7, pBLapr comprises a 6.1 kb plasmid including the ampicillin resistance gene from pBR322 and the chloramphenicol resistance gene from pC194, the aprE promoter and the gene encoding for the *Bacillus licheniformis* α-amylase ("BL AA"). The aprE promoter was constructed from a 660 bp HindIII-PstI fragment encoding for the promoter and signal sequence of the *Bacillus subtilis* alkaline protease. The PstI site was removed, and an SfiI site added close to the aprE/BL AA junction. The BL AA gene comprises the 1720 bp PstI-Sstl fragment described above. In the work described herein, pBLapr was constructed with an SfiI site adjacent to the 5' end of the start of the coding sequence for the mature amylase gene. Specifically, the 5' end of the pBLapr construction was subcloned on an EcoRI-SstII fragment from pBLapr into M13BM20 (Boehringer Mannheim) to obtain a coding-strand template for the mutagenic oligonucleotide below:

This primer introduced an SfiI site (indicated by underlining) which allowed correct forms to be screened for by the presence of this unique restriction site. Subcloning the EcoRI-SstII fragment back into the pBLapr vector gave a version of the plasmid containing an SfiI site.

Plasmid pHP13 (Haima et al., Mol. Gen. Genet., vol. 209, pp. 335–342 (1987)) (FIG. 6) was digested with restriction enzymes EcoRI and HindIII and the resulting vector purified on a polyacrymide gel and then eluted. Plasmid pBLapr was digested with HindIII, Asp718 and in a separate incubation with Asp718, EcoRI and gel purified. Two bands, HindIII -Asp718 (1203 bp) and Asp718-EcoRI (1253 bp) were gel purified, eluted from the gel and ligated into the vector by a 3-way ligation, to give plasmid pHP.BL, the plasmid used in expression of the α-amylase (FIG. 8).

Example 2

Construction of Plasmid Encoding α-Amylase Comprising Substitutions for Asparagine 188

A series of mutagenic primers encoding for substitutions of Asn188 ("N188") with each of the naturally occurring amino acids were synthesized and are shown in FIG. 1 (SEQ ID NOS:4–22). The α-amylase gene mutations encoding for these changes were made by PCR, according to the procedure summarized in FIG. 9, using the PCR primers shown in FIG. 2 (SEQ ID NOS:23–32).

Step (1)

The mutagenic primers were used as templates for the PCR primers PCR A+ and PCR B– resulting in a lengthened (61 bp) double stranded DNA. Each contained a different amino acid replacement at position 188, and all except N188M contained a different restriction site. Initially the PCR primers were annealed at 35° C. for five minutes followed by a one minute DNA extension with taq polymerase at 75° C. The double stranded DNA was then melted at 95° C. for one minute, followed by the annealing and extension steps. Melting, annealing and extension continued for a total of 30 cycles.

Step (2)

DNA upstream and downstream of position 188 were made in separate PCR reactions. The template was pBLapr, and the PCR primers were LAAfs5 (SEQ ID NO:27) and PCR A– (SEQ ID NO:24) for upstream; and PCR B+ (SEQ ID NO:25) and PCR ClaI-SalI (SEQ ID NO:28) for downstream DNA. The DNA was melted at 95° C. for one minute, annealed at 45° C. for three minutes and elongated at 68° C. for 3 minutes. The upstream portion is 290 bp and downstream is 498 bp. This procedure was repeated for 18 cycles using pfu polymerase. The same PCR procedure was used in steps (3) and (4).

Step (3)

The upstream portion of DNA described in step (2) was attached to the double stranded mutagenic primers described in step (1). Primers LAAfs5 (SEQ ID NO:27) and PCR B– (SEQ ID NO:26) were used. As the result of primer design

```
5'-CCC ATT AAG ATT GGC CGC CTG GGC CGA CAT GTT GCT GG-3' (SEQ ID NO:3)
``` there is a 24 bp overlap between these templates allowing for the attachment of the two pieces of DNA.

Step (4)

The downstream portions of DNA described in Step (2) and the product of Step (3) were attached to give the final product. A 24 bp overlap between the two PCR products allows for the attachment. Primers used were LAAfs5 (SEQ ID NO:27) and PCR ClaI-SalI (SEQ ID NO:28).

Step (5)

Unique restriction sites, Asp718 and BssHII, are located upstream and downstream, respectively, of the 188 site. The final PCR product is digested with Asp718 and BssHII, the 333 bp fragment isolated by polyacrylamide gel electrophoresis and subcloned into the pHP.BL vector to obtain pHP.N188X.

Mutations were confirmed by dideoxy sequencing (Sanger et al., Proc. Natl. Acad. Sci. U.S.A., vol. 74, pp. 5463–5467 (1977)).

With reference to the DNA sequence and numbering system used in FIG. 3, the codon encoding for the +188 amino acid position is at base pairs 812–814. PCR primers A+ and A− correspond to base pairs 784–807. PCR primers B+ and B− correspond to base pairs 821–844. The 5' end of PCR primer LAAfs5 corresponds to base pair 518. The 5' end of PCR primer PCR ClaI-SalI corresponds to base pair 1317. The Asp718 site corresponds to base pair 724. The BssHII site corresponds to base pair 1053.

Example 3

Construction of Plasmid Encoding Mutations at M15 and N188

A pBLapr plasmid having threonine substituted for methionine at amino acid 15 was constructed according to U.S. patent application Ser. No. 08/194,664 (PCT Publication No. WO 94/18314). This plasmid (pBLaprM15T) was digested with SfiI and Asp718, and the 477 base pair fragment subcloned into pHP.BL to create pHP.M15T. In a manner analogous to that described above, Example 1, pHP.M15T was digested with Asp718 and BssHII, gel purified and eluted from the gel. The 333 base pair fragment comprising Asp718 to BssHII and the fragment from pHP.N188S were then subcloned into pHP.M15T to give plasmid pHP.M15T/N188S. In an analogous manner, starting with plasmids pBL aprM15L and pHP.N188Y, the plasmid pHP.M15L/N188Y was constructed.

Example 4

Transformation of Plasmids into *Bacillus subtilis*, Expression and Purification of Mutant α-Amylase α-Amylase was expressed in *Bacillus subtilis* after transformation with the plasmids described in Examples 1–3. pHP13 is a plasmid able to replicate in *E. coli* and in *Bacillus subtilis*. Plasmids containing different variants were constructed using *E. coli* strain MM294, the plasmids isolated and then transformed into *Bacillus subtilis* as described in Anagnostopoulos et al., J. Bacter., vol. 81, pp. 741–746 (1961). The Bacillus strain had been deleted for two proteases (Δapr, Δnpr) (see e.g., Ferrari et al., U.S. Pat. No. 5,264,366) and for amylase (ΔamyE) (see e.g., Stahl et al., J. Bacter., vol. 158, pp. 411–418 (1984)). The bacillus strain expressing M15L/N188Y was found to form larger zones of clearing than the strain expressing M15L on agar plates containing 1% insoluble starch indicating increased amylolytic activity. After transformation, the sacU(Hy) mutation (Henner et al., J. Bacter., vol., 170, pp. 296–300 (1988)) was introduced by PBS-1 mediated transduction (Hoch, J. Bact., vol. 154, pp. 1513–1515 (1983)).

Secreted amylases were routinely recovered from *Bacillus subtilis* cultures as follows: The culture supernatant was adjusted to 20% saturated ammonium sulfate and stirred for one hr. at 4° C. After centrifugation, the resultant supernatant was adjusted to 70% saturated ammonium sulfate and stirred for one hr. at 4° C. After centrifugation of the supernatant, the resultant pellet was re-dissolved in 50 mM sodium acetate, pH 6.0, 5 mM calcium chloride, and sterile filtered.

Example 5

Assay for Determining α-Amylase Activity

Soluble Substrate Assay

A rate assay was developed based on an end-point assay kit supplied by Megazyme (Aust.) Pty. Ltd. A vial of substrate (p-nitrophenyl maltoheptaoside, BPNPG7) was dissolved in 10 ml of sterile water followed by a 1:4 dilution in assay buffer (50 mM maleate buffer, pH 6.7, 5 mM calcium chloride, 0.002% Tween20). Assays were performed by adding 10 μl of amylase to 790 μl of the substrate in a cuvette at 25° C. Rates of hydrolysis were measured as the rate of change of absorbance at 410 nm, after a delay of 75 seconds. The assay was linear up to rates of 0.2 absorption units/min.

α-Amylase protein concentration was measured using the standard Bio-Rad Assay (Bio-Rad Laboratories) based on the method of Bradford, Anal. Biochem., vol. 72, p. 248 (1976) using bovine serum albumin standards.

Starch Hydrolysis Assay

α-Amylase activity on starch was determined through an assay which depends on the ability of starch to form a blue colored complex with iodine and the disappearance of this color when starch is hydrolyzed to shorter dextrin molecules. The α-amylase activity was defined in terms of the digestion time required to produce a color change denoting a definite state of dextrination of the starch.

Reagents used were as follows:

Phosphate buffer—Potassium dihydrogen phosphate (340 g) and sodium hydroxide (25.3 g) were dissolved in water and diluted to ~two liters. The buffer was cooled to room temperature and the pH was adjusted to 6.2±0.1. The buffer was diluted to two liters in a volumetric flask.

Starch substrate—Ten grams (dry substance) of soluble lintner starch were suspended in 50 ml of water and washed into ~300 ml of boiling water. The suspension was again brought to boiling and was boiled for five minutes with constant stirring. The starch solution was cooled with constant stirring to room temperature and 125 ml of phosphate buffer was added. The solution was diluted to 500 ml with water. The starch substrate was made fresh daily.

Stock iodine solution—Iodine crystals (5.5 g) and potassium iodide (11.0 g) were dissolved in water and were volumetrically diluted to 250 ml. The solution was kept from light.

Dilute iodine solution—Potassium iodide (20 g) and two ml of stock iodine solution were dissolved in water and diluted volumetrically to 500 ml. The solution was made fresh daily.

Enzyme diluting solution—Calcium chloride (11.1 g) was dissolved in four liters of water. Water used for all reagents was either distilled or deionized.

An α-amylase sample was diluted to between 10–15 LU/ml (as defined below) with enzyme diluting solution. For many commercial α-amylase preparations a suitable dilution was found to be 2000 fold. Five milliliter aliquots of dilute iodine solution were dispensed into 13×100 mm test tubes and 10 ml of starch substrate was placed in a 23×200 mm test tube. All tubes were placed in the 30° C. water bath. A Hellige comparator equipped with a special α-amylase color disc (catalog number 620-s5) was used to make readings. Five milliliters of diluted enzyme (also at 30° C.) were mixed with the starch substrate and timing was begun. At appropriate time intervals, for example one minute intervals early in the reaction and 15 second intervals later in the reaction, one ml aliquots of the enzyme-substrate mixture were transferred to a tube containing the dilute iodine solution. The starch iodine solution was mixed and transferred to a 13 mm precision square tube and the color was compared with the standard α-amylase color disc in the Hellige comparator. When the time of the end point was approached, samples were taken at 0.25 minute intervals.

The time required for the colors of the samples and the color disc to match were recorded and the activity (in liquefons per gram or ml) was calculated according to the formula:

$$LU/ml \text{ or } LU/g = \left\{ \frac{570}{V \times t} \right\} \times D$$

Where:

LU=liquefon unit

V=volume of enzyme (5 ml or grams)

t=dextrinization time (minutes)

D=dilution factor: dilution volume divided by ml or g of enzyme diluted.

Mutant α-amylases according to the invention prepared as in Examples 1–4 were tested for their specific activity on starch and soluble substrate. The results, as shown in Table 1, illustrate that mutant amylase according to the invention provides a superior activity profile in comparison with the AA20 wild type α-amylase on both substrates.

TABLE 1

Specific Activity Of Certain α-Amylases On Soluble Substrate And Starch As Percentage Of Wild Type Activity

| α-AMYLASE | Soluble Substrate Assay | Starch Hydrolysis Assay |
| --- | --- | --- |
| Spezyme ® AA20 | 100 | 100 |
| M15T/N188S | 212 | 166 |

Example 6

Starch Liquefaction Conditions—Determination of Liquefied Starch DE (Dextrose Equivalent)

Starch liquefaction was performed using a reactor composed of 50 feet of 0.24 inch diameter (0.21 inch i.d.) stainless steel tubing bent into an approximately 10 inch diameter coil ~5.5 inches high. The coil was equipped with an 11.5 inch in-line static mixer (Cole-Parmer #G-04669-60) mounted ~4 feet from the anterior end. The posterior end of the coil was equipped with a Swagelok in-line adjustable pressure relief value (#SS-4CA-3) set at a cracking pressure of about 20 psi. Starch slurry was fed to the coil at a rate of ~70 ml/minute with a piston metering pump. The temperature of the reactor coil was held at 105.5° C. by immersion of the reactor in a glycerol-water bath. Temperature in the bath was maintained using a circulating heater/temperature controller (Fisher Scientific model 7305).

Starch liquefaction at the pilot scale was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve. Starch was introduced into the jet at about 350 ml/min. The jet temperature was held at 105–107° C. Samples of starch were transferred from the jet cooker to a 95° C. second stage liquefaction and held for 90 minutes.

Granular starch was obtained from a corn wet miller and used within two days. The starch was diluted to a desired solids level of about 30–35% dry solids with deionized water and the pH was adjusted with 2.5% NaOH or 6% HCl as required. Calcium was added in the form of $CaCl_2 \cdot 2H_2O$. Typical liquefaction conditions were:

| | |
| --- | --- |
| Starch | 30%–35% solids |
| Calcium | 40–60 ppm (30 ppm added) |
| pH | 5.0–6.0 |
| α-amylase | 12–14 LU/g of carbohydrate (dry basis) |

Samples of starch were transferred from the reactor to a 95° C. second stage liquefaction bath and held for 90 minutes. The degree of starch liquefaction was measured immediately after the second stage liquefaction by determining the dextrose equivalent (DE) of the sample according to the method described in the *Standard Analytical Methods of the Member Companies of the Corn Refiners Association, Inc.*, sixth ed., Analytical Procedure Committee (1980).

Example 7

Comparison of M15T/N188S and Wild Type α-Amylase in Liquefaction at 105.5° C.

α-Amylase comprising the substitution M15T/N188S made as per Examples 1–4 was compared with wild type α-amylase derived from *Bacillus licheniformis* (Spezyme® AA20, available commercially from Genencor International, Inc.) in liquefaction at 105.5° C. As shown in Table 2, the mutant enzymes provided significantly increased performance in jet-liquefaction of starch, especially at low pH. Pilot scale liquefaction was performed with a primary stage liquefaction at 105.5° C. and a secondary stage liquefaction at 95° C. Amylase was added at 12 LU/g of carbohydrate (dry basis).

TABLE 2

Comparative Liquefaction Performance Of α-Amylases At 105.5° C.

| AMYLASE | pH | DE |
| --- | --- | --- |
| Spezyme ® AA20 (Average of Two Runs) | 6.0 | 9.85 |
| G11 (Average of Four Runs) | 6.0 | 12.2 |
| Spezyme ® AA20 | 5.5 | 5.4 |
| G11 (Average of Two Runs) | 5.5 | 8.7 |
| Spezyme ® AA20 | 5.2 | 1.8 |
| G11 | 5.2 | 3.0 |

Example 8

Comparison of M15T/N188S and Wild Type α-Amylase in Liquefaction at 107.0° C.

α-Amylase comprising substitution M15T/N188S made as per Examples 1–4 was compared with wild type α-amylase derived from *Bacillus licheniformis* (Spezyme® AA20, available commercially from Genencor International, Inc.) in liquefaction at 107° C. As shown in Table 3, the mutant enzymes provided significantly increased performance in jet-liquefaction of starch especially at low pH, as shown by the DE value, during liquefaction processes. Pilot scale liquefaction was performed with a primary stage liquefaction at 107° C. and a secondary stage liquefaction at 95° C. Amylase was added at 12 LU/g or carbohydrate (dry basis).

TABLE 3

Comparative Liquefaction Performance of α-Amylase At 107° C.

| VARIANT | pH | DE |
|---|---|---|
| AA20 | 6.0 | 7.4 |
| G11 | 6.0 | 11.6 |
| AA20 | 5.5 | 3.5 |
| G11 | 5.5 | 6.0 |
| AA20 | 5.2 | 0 |
| G11 | 5.2 | 1.1 |

Example 9

Statistical Analysis of Liquefaction Results for Mutant and Wild Type α-Amylase

The relative liquefaction performance of Spezyme® AA20 and the M15T/N188S variant were extensively explored in a statistical design experiment. Using the "X-STAT" program, Version 2.0 (Copyright, Wiley Scientific and Technical Software, John Wiley & Sons, New York, (1992)), a Box-Behnken factorial experiment was designed; varying the primary liquefaction temperature from 106° C. to 110° C., the liquefaction pH from pH 5.3 to pH 6.0, and the total calcium level in the starch substrate from 30 ppm to 90 ppm. The data in Tables 4 and 5 which formed the basis of this experiment was generated in 15 pilot scale liquefactions each, using 12 LU/gram dry solid substrate of Spezyme® AA20 and M15T/N188S. The data was then fitted to quadratic models. For the M15T/N188S variant, the data fitted the equation DE=842.41+28.374×pH−17.557 ×Temperature+1.5005×Calcium concentration+1.6243 (pH×Temperature)−0.081506 (pH×Calcium concentration)−0.0092099 (Temperature×Calcium concentration)−16.841 (pH)$^2$+0.038379 (Temperature)$^2$−0.000124 (Calcium concentration)$^2$ with a standard error about the regression of 1.313 and an explained variation about the mean (R)$^2$ of 93.99%. For Spezyme® AA20, the data was fitted to the equation DE=−652.0+(132.35×pH)+(4.716×Temperature)+(1.3989×Calcium concentration)−0.050515 (pH× Temperature)−0.019603 (pH×Calcium concentration)−0.011118 (Temperature×Calcium concentration)−10.206 (pH)$^2$+0.02104 (Temperature)$^2$−0.000522 (Calcium concentration)$^2$. With a standard error about the regression of 0.5772 and an explained variation about the mean (R$^2$) of 98.69%, these equations were used to prepare curves plotting calculated DE vs. pH, vs. Calcium concentration vs. Temperature. Two dimensional representations of that data at 107° C. and 60 ppm Ca+ are illustrated in FIGS. 10–12 respectively. As shown in FIGS. 10–12, the mutant amylase outperforms the wild type amylase by enabling more efficient liquefaction of starch at lower pH, lower levels of calcium and higher temperature.

TABLE 4

| pH | Temperature Celsius | Calcium ppm | Observed Dextrose Equivalent M15T/N188S |
|---|---|---|---|
| 6.00 | 110.2 | 60.0 | 9.8 |
| 6.00 | 105.9 | 60.0 | 11.7 |
| 5.30 | 110.2 | 60.0 | 2.1 |
| 5.30 | 106.5 | 60.0 | 8.1 |
| 6.00 | 108.0 | 90.0 | 11.3 |
| 6.00 | 107.6 | 30.0 | 10.3 |
| 5.30 | 108.4 | 90.0 | 5.9 |
| 5.30 | 108.5 | 30.0 | 1.7 |
| 5.65 | 110.2 | 90.0 | 9.5 |
| 5.65 | 109.8 | 30.0 | 9.9 |
| 5.65 | 106.0 | 90.0 | 11.9 |
| 5.65 | 105.5 | 30.0 | 9.9 |
| 5.65 | 107.8 | 60.0 | 9.5 |
| 5.65 | 108.1 | 60.0 | 9.6 |
| 6.00 | 108.3 | 60.0 | 11.6 |

TABLE 5

| pH | Temperature Celsius | Calcium ppm | Observed Dextrose Equivalent Spezyme ® AA20 |
|---|---|---|---|
| 6.00 | 110.0 | 60 | 7.4 |
| 6.00 | 106.2 | 60 | 9.9 |
| 5.30 | 109.7 | 60 | 0.6 |
| 5.30 | 105.8 | 60 | 2.9 |
| 6.00 | 108.3 | 90 | 8.5 |
| 6.00 | 108.4 | 30 | 7.8 |
| 5.30 | 108.6 | 90 | 1.2 |
| 5.30 | 107.5 | 30 | 0.4 |
| 5.65 | 110.0 | 90 | 4.1 |
| 5.65 | 109.5 | 30 | 4.0 |
| 5.65 | 106.8 | 90 | 8.6 |
| 5.65 | 106.0 | 30 | 6.4 |
| 5.65 | 107.8 | 60 | 6.1 |
| 5.65 | 109.0 | 60 | 5.9 |
| 5.65 | 109.0 | 60 | 5.9 |

While the invention has been described in terms of various preferred embodiments, the skilled artisan will appreciate that various modifications, substitutions, omissions and changes may be made without departing from the spirit and scope thereof. Accordingly, it is intended that the scope of the present invention be limited solely by the scope of the following claims, including equivalents thereof.

Example 10

Preparation and Testing of Additional Mutant Alpha-Amylases for Thermal Stability Mutant alpha-amylases were prepared having substitutions at one or more of positions V128E, H133Y, S187D and/or A209V generally according to the procedures provided in Examples 1–4 except that appropriate PCR primers were provided to effect the desired mutations. Amylases were purified to a point where wild type *Bacillus licheniformis* α-amylase showed a specific activity of 1087 LU/mg protein. Protein concentration was determined by absorption at 278 nm, using a Molar Extinction coefficient of wild type enzyme of 143,255 M$^{-1}$ cm$^{-1}$.

Thermal inactivation rates for the various mutants were measured according to the following procedure. Amylase stock solutions were dialysed extensively into 20 mM ammonium acetate, 4 mM CaCl$_2$ pH 6.5. For measurement of stability, this stock was diluted >50 fold into 50 mM ammonium acetate, 5mM CaCl$_2$, 0.02% Tween 20 pH 5.0 to a final concentration of between 30 and 50 µg/ml. Six 100 µl aliquots were put into eppendorf tubes and placed into a water bath at 83° C. The eppendorf tubes were removed at regular, measured intervals of between 30 seconds and 5 minutes and placed on ice to stop the inactivation. The residual activity was assayed using a soluble substrate as described in Example 5. The natural log of the activity was plotted against time of incubation, and the rate constant for inactivation obtained from the slope of the straight line. Results for various mutants are provided in Table 6.

TABLE 6

| Amylase | Inactivation Rate Constant, k(min$^{-1}$) | Half Life (ln2/k) (min) | Improvement Over Wild Type |
|---|---|---|---|
| Wild Type | 1.2 | 0.56 | 1.0 |
| M15T/N188S | 0.81 | 0.86 | 1.5 |
| M15L/N188S | 0.76 | 0.91 | 1.6 |
| M15T/H133Y | 0.39 | 1.8 | 3.2 |
| M15T/H133Y/N188S | 0.31 | 2.2 | 4.0 |
| M15T/N188S/A209V | 0.27 | 2.5 | 4.5 |
| M15T/H133Y/N188S/A209V | 0.054 | 13 | 23 |

Example 11

Low pH Liquefaction Performance of Variant α-Amylases

α-Amylase comprising substitutions M15T/N188S or M15T/H133Y/N188S were made as per Examples 1–4 and 10 and compared in liquefaction studies as per Example 6. Liquefaction was performed at 105.5° C. with a secondary hold of 90 minutes at 95° C. under conditions including 94 ppm SO$_2$ with amylase at a concentration of 16 LU/g of carbohydrate (dry basis). The results are provided in Table 7 below.

TABLE 7

| Amylase | pH | DE |
|---|---|---|
| M15T/N188S | 5.50 | 11.6 |
| M15T/H133Y/N188S | 5.50 | 13.9 |
| M15T/N188S | 5.35 | 7.8 |
| M15T/H133Y/N188S | 5.35 | 10.0 |
| M15T/N188S | 5.20 | 3.2 |
| M15T/H133Y/N188S | 5.20 | 5.0 |

Example 12

Low pH Liquefaction Performance of M15T/V128E/H133Y/N188S, M15T/H133Y/N188S and M15T/N188S at Varying Calcium Levels α-Amylase comprising various substitutions were made as per Examples 14 and 10 and compared in liquefaction studies as per Example 6. Liquefaction was performed at 105.5° C. under conditions including a pH of 5.50, 95 ppm SO$_2$ with amylase at a concentration of 12 LU/g of carbohydrate (dry basis). The results are provided in Table 8 below.

TABLE 8

| Amylase | Calcium Added | DE |
|---|---|---|
| M15T/V128E/H133Y/N188S | 44 | 11.8 |
| M15T/H133Y/N188S | 44 | 12.4 |
| M15T/N188S | 44 | 9.9 |
| M15T/V128E/H133Y/N188S | 0 | 8.9 |
| M15T/H133Y/N188S | 0 | 7.6 |
| M15T/N188S | 0 | 4.9 |

Example 13

Low pH Liquefaction Performance of M15T/H133Y and M15T/H133Y/A209V at Varying pH Levels α-Amylase comprising various substitutions were made as per Examples 1–4 and 10 and compared in liquefaction studies as per Example 6. Liquefaction was performed at 105.5° C. under conditions including 98 ppm SO$_2$ with amylase at a concentration of 19 LU/g of carbohydrate (dry basis). Dried corn starch (Clinton Brand 106-B Pearl cornstarch, ADM Corn Processing, Clinton, Iowa) was slurried with deionized water (~23 kg in ~50 liters) and allowed to hydrate for 16 hours. The results are provided in Table 9 below.

TABLE 9

| Amylase | pH | DE |
|---|---|---|
| M15T/H133Y/N188S | 5.00 | 6.8 |
| M15T/H133Y/N188S/A209V | 5.00 | 10.0 |
| M15T/H133Y/N188S | 5.25 | 11.6 |
| M15T/H133Y/N188S/A209V | 5.25 | 13.2 |
| M15T/H133Y/N188S | 5.50 | 14.3 |
| M15T/H133Y/N188S/A209V | 5.50 | 15.9 |

Example 14

Improved Liquefaction Performance of Variant α-Amylase Compared to Wild Type

α-Amylase comprising substitution at M15T/S187D/N188S were made as per Examples 1–4 and 10 and compared to wild type in liquefaction studies as per Example 6. Dried corn starch (Clinton Brand 106-B Pearl cornstarch, ADM Corn Processing, Clinton, Iowa) was slurried with deionized water (~23 kg in ~50 liters) and allowed to hydrate for 16 hours. Liquefaction was performed at 105.6° C. with equal protein levels of amylase at 9.0 µg amylase/g carbohydrate (dry basis) (3.1 mg amylase/liter of 35% dry solid starch slurry). Due to the specific activity benefit derived from the mutant alpha amylase, the activity of the amylases was 11 LU/g carbohydrate (dry basis) for the wild type amylase and 24 LU/g carbohydrate for the mutant. Measured activities showed that the mutant amylase had an activity increase of 410% of the wild type on heptamaltose and 219% of the wild type on starch. The liquefaction results are provided in Table 10 below.

TABLE 10

| Amylase | pH | DE |
|---|---|---|
| Wild Type | 6.00 | 8.9 |
| M15T/S187D/N188S | 6.00 | 11.2 |

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
      (A) LENGTH: 56 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GATCAAAACA TAAAAAACCG GCCTTGGCCC CGCCGGTTTT TTATTATTTT TGAGCT     56

(2) INFORMATION FOR SEQ ID NO: 2:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

CAAAAATAAT AAAAAACCGG CGGGGCCAAG GCCGGTTTTT TATGTTTT     48

(2) INFORMATION FOR SEQ ID NO: 3:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

CCCATTAAGA TTGGCCGCCT GGGCCGACAT GTTGCTGG     38

(2) INFORMATION FOR SEQ ID NO: 4:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 4:

GGATTGGGAA GTGTCGACTG AAAACGGCAA CTATGAT     37

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GGATTGGGAA GTTTCCCCAG AAAATGGCAA CTATGAT                                37
```

(2) INFORMATION FOR SEQ ID NO: 6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
GGATTGGGAA GTTTCTAGAG AAAACGGCAA CTATGAT                                37
```

(2) INFORMATION FOR SEQ ID NO: 7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GGATTGGGAA GTTTCCCTCG AGAACGGCAA CTATGAT                                37
```

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
GGATTGGGAA GTTTCGGCCG AAAACGGCAA CTATGAT                                37
```

(2) INFORMATION FOR SEQ ID NO: 9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
GGATTGGGAA GTTTCCGGAG AAAACGGCAA CTATGAT                                37
```

(2) INFORMATION FOR SEQ ID NO: 10:

(i) SEQUENCE CHARACTERISTICS:
        (A) LENGTH: 37 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGATTGGGAA GTTTCCAAGG AAAACGGCAA CTATGAT                37

(2) INFORMATION FOR SEQ ID NO: 11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GGATTGGGAA GTTTCCCAGG AAAATGGCAA CTATGAT                37

(2) INFORMATION FOR SEQ ID NO: 12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GGATTGGGAA GTTTCCCAGG AAAATGGCAA CTATGAT                37

(2) INFORMATION FOR SEQ ID NO: 13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGATTGGGAA GTTTCTCATG AAAACGGCAA CTATGAT                37

(2) INFORMATION FOR SEQ ID NO: 14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GGATTGGGAA GTTTCCGAAG AGAACGGCAA CTATGAT                37

(2) INFORMATION FOR SEQ ID NO: 15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GGATTGGGAA GTTTCCGAGG AGAACGGCAA CTATGAT                    37

(2) INFORMATION FOR SEQ ID NO: 16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GGATTGGGAA GTTTCATATG AAAACGGCAA CTATGAT                    37

(2) INFORMATION FOR SEQ ID NO: 17:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GGATTGGGAA GTCTCCTGCG AAAACGGCAA CTATGAT                    37

(2) INFORMATION FOR SEQ ID NO: 18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GGATTGGGAA GTTTCCTTCG AAAACGGCAA CTATGAT                    37

(2) INFORMATION FOR SEQ ID NO: 19:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GGATTGGGAA GTTTCGATCG AAAACGGCAA CTATGAT                    37

(2) INFORMATION FOR SEQ ID NO: 20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GGATTGGGAA GTTTCCATGG AAAACGGCAA CTATGAT                    37

(2) INFORMATION FOR SEQ ID NO: 21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

GGATTGGGAA GTTTCCTGGG AAAACGGCAA CTATGAT                    37

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GGATTGGGAA GTGAGCTCTG AAAACGGCAA CTATGAT                    37

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

AGGAAAGGCT TGGGATTGGG AAGT                                 24

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

ACTTCCCAAT CCCAAGCCTT TCCT                                 24

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GGCAACTATG ATTATTTGAT GTAT                                 24

(2) INFORMATION FOR SEQ ID NO: 26:

(i) SEQUENCE CHARACTERISTICS:
        (A) LENGTH: 24 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 26:

ATACATCAAA TAATCATAGT TGCC                                              24

(2) INFORMATION FOR SEQ ID NO: 27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 27:

CTTCATTCCC GCGACATTAA C                                                 21

(2) INFORMATION FOR SEQ ID NO: 28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 28:

GATTCCCTTG TGAGAATAAA AG                                                22

(2) INFORMATION FOR SEQ ID NO: 29:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 29:

AATCATGTCA GGGAAAAAAC TGGG                                              24

(2) INFORMATION FOR SEQ ID NO: 30:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 30:

CCCAGTTTTT TCCCTGACAT GATT                                              24

(2) INFORMATION FOR SEQ ID NO: 31:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 31:

TTTACGGTAG CTGAATATTG GCAG    24

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

CTGCCAATAT TCAGCTACCG TAAA    24

(2) INFORMATION FOR SEQ ID NO: 33:

(i) SEQUENCE CHARACTERISTICS:
        (A) LENGTH: 1968 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 33:

```
AGCTTGAAGA AGTGAAGAAG CAGAGAGGCT ATTGAATAAA TGAGTAGAAA GCGCCATATC    60
GGCGCTTTTC TTTTGGAAGA AAATATAGGG AAAATGGTAC TTGTTAAAAA TTCGGAATAT   120
TTATACAACA TCATATGTTT CACATTGAAA GGGGAGGAGA ATCATGAAAC AACAAAAACG   180
GCTTTACGCC CGATTGCTGA CGCTGTTATT TGCGCTCATC TTCTTGCTGC CTCATTCTGC   240
AGCAGCGGCG GCAAATCTTA ATGGGACGCT GATGCAGTAT TTTGAATGGT ACATGCCCAA   300
TGACGGCCAA CATTGGAAGC GTTTGCAAAA CGACTCGGCA TATTTGGCTG AACACGGTAT   360
TACTGCCGTC TGGATTCCCC CGGCATATAA GGGAACGAGC CAAGCGGATG TGGGCTACGG   420
TGCTTACGAC CTTTATGATT TAGGGGAGTT TCATCAAAAA GGGACGGTTC GGACAAAGTA   480
CGGCACAAAA GGAGAGCTGC AATCTGCGAT CAAAAGTCTT CATTCCCGCG ACATTAACGT   540
TTACGGGGAT GTGGTCATCA ACCACAAAGG CGGCGCTGAT GCGACCGAAG ATGTAACCGC   600
GGTTGAAGTC GATCCCGCTG ACCGCAACCG CGTAATTTCA GGAGAACACC TAATTAAAGC   660
CTGGACACAT TTTCATTTTC CGGGGCGCGG CAGCACATAC AGCGATTTTA AATGGCATTG   720
GTACCATTTT GACGGAACCG ATTGGGACGA GTCCCGAAAG CTGAACCGCA TCTATAAGTT   780
TCAAGGAAAG GCTTGGGATT GGGAAGTTTC CAATGAAAAC GGCAACTATG ATTATTTGAT   840
GTATGCCGAC ATCGATTATG ACCATCCTGA TGTCGCAGCA GAAATTAAGA GATGGGGCAC   900
TTGGTATGCC AATGAACTGC AATTGGACGG TTTTCGTCTT GATGCTGTCA ACACATTAA    960
ATTTTCTTTT TTGCGGGATT GGGTTAATCA TGTCAGGGAA AAACGGGGA AGGAAATGTT   1020
TACGGTAGCT GAATATTGGC AGAATGACTT GGGCGCGCTG GAAAACTATT TGAACAAAAC  1080
AAATTTTAAT CATTCAGTGT TTGACGTGCC GCTTCATTAT CAGTTCCATG CTGCATCGAC  1140
ACAGGGAGGC GGCTATGATA TGAGGAAATT GCTGAACGGT ACGGTCGTTT CCAAGCATCC  1200
GTTGAAATCG GTTACATTTG TCGATAACCA TGATACACAG CCGGGGCAAT CGCTTGAGTC  1260
GACTGTCCAA ACATGGTTTA AGCCGCTTGC TTACGCTTTT ATTCTCACAA GGGAATCTGG  1320
ATACCCTCAG GTTTTCTACG GGGATATGTA CGGGACGAAA GGAGACTCCC AGCGCGAAAT  1380
TCCTGCCTTG AAACACAAAA TTGAACCGAT CTTAAAAGCG AGAAACAGT ATGCGTACGG   1440
```

```
AGCACAGCAT GATTATTTCG ACCACCATGA CATTGTCGGC TGGACAAGGG AAGGCGACAG    1500

CTCGGTTGCA AATTCAGGTT TGGCGGCATT AATAACAGAC GGACCCGGTG GGGCAAAGCG    1560

AATGTATGTC GGCCGGCAAA ACGCCGGTGA GACATGGCAT GACATTACCG GAAACCGTTC    1620

GGAGCCGGTT GTCATCAATT CGGAAGGCTG GGGAGAGTTT CACGTAAACG GCGGGTCGGT    1680

TTCAATTTAT GTTCAAAGAT AGAAGAGCAG AGAGGACGGA TTTCCTGAAG GAAATCCGTT    1740

TTTTTATTTT GCCCGTCTTA TAAATTTCTT TGATTACATT TTATAATTAA TTTTAACAAA    1800

GTGTCATCAG CCCTCAGGAA GGACTTGCTG ACAGTTTGAA TCGCATAGGT AAGGCGGGGA    1860

TGAAATGGCA ACGTTATCTG ATGTAGCAAA GAAAGCAAAT GTGTCGAAAA TGACGGTATC    1920

GCGGGTGATC AATCATCCTG AGACTGTGAC GGATGAATTG AAAAAGCT                 1968
```

(2) INFORMATION FOR SEQ ID NO: 34:

(i) SEQUENCE CHARACTERISTICS:
        (A) LENGTH: 483 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 34:

```
Ala Asn Leu Asn Gly Thr Leu Met Gln Tyr Phe Glu Trp Tyr Met Pro
 1               5                  10                  15

Asn Asp Gly Gln His Trp Lys Arg Leu Gln Asn Asp Ser Ala Tyr Leu
             20                  25                  30

Ala Glu His Gly Ile Thr Ala Val Trp Ile Pro Pro Ala Tyr Lys Gly
         35                  40                  45

Thr Ser Gln Ala Asp Val Gly Tyr Gly Ala Tyr Asp Leu Tyr Asp Leu
     50                  55                  60

Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255
```

```
Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg (2) INFORMATION FOR SEQ ID NO: 35:

(i) SEQUENCE CHARACTERISTICS:
        (A) LENGTH: 511 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 35:

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
        35                  40                  45

His Trp Lys Arg Leu Gln Asn Asp Ser Ala Tyr Leu Ala Glu His Gly
    50                  55                  60

Ile Thr Ala Val Trp Ile Pro Pro Ala Tyr Lys Gly Thr Ser Gln Ala
65                  70                  75                  80

Asp Val Gly Tyr Gly Ala Tyr Asp Leu Tyr Asp Leu Gly Glu Phe His
                85                  90                  95

Gln Lys Gly Thr Val Arg Thr Lys Tyr Gly Thr Lys Gly Glu Leu Gln
            100                 105                 110

Ser Ala Ile Lys Ser Leu His Ser Arg Asp Ile Asn Val Tyr Gly Asp
        115                 120                 125
```

Val Val Ile Asn His Lys Gly Gly Ala Asp Ala Thr Glu Asp Val Thr
    130                 135                 140

Ala Val Glu Val Asp Pro Ala Asp Arg Asn Arg Val Ile Ser Gly Glu
145                 150                 155                 160

His Leu Ile Lys Ala Trp Thr His Phe His Phe Pro Gly Arg Gly Ser
                165                 170                 175

Thr Tyr Ser Asp Phe Lys Trp His Trp Tyr His Phe Asp Gly Thr Asp
            180                 185                 190

Trp Asp Glu Ser Arg Lys Leu Asn Arg Ile Tyr Lys Phe Gln Gly Lys
        195                 200                 205

Ala Trp Asp Trp Glu Val Ser Asn Glu Asn Gly Asn Tyr Asp Tyr Leu
    210                 215                 220

Met Tyr Ala Asp Ile Asp Tyr Asp His Pro Asp Val Ala Ala Glu Ile
225                 230                 235                 240

Lys Arg Trp Gly Thr Trp Tyr Ala Asn Glu Leu Gln Leu Asp Gly Phe
                245                 250                 255

Arg Leu Asp Ala Val Lys His Ile Lys Phe Ser Phe Leu Arg Asp Trp
            260                 265                 270

Val Asn His Val Arg Glu Lys Thr Gly Lys Glu Met Phe Thr Val Ala
        275                 280                 285

Glu Tyr Trp Gln Asn Asp Leu Gly Ala Leu Glu Asn Tyr Leu Asn Lys
290                 295                 300

Thr Asn Phe Asn His Ser Val Phe Asp Val Pro Leu His Tyr Gln Phe
305                 310                 315                 320

His Ala Ala Ser Thr Gln Gly Gly Gly Tyr Asp Met Arg Lys Leu Leu
                325                 330                 335

Asn Gly Thr Val Val Ser Lys His Pro Leu Lys Ser Val Thr Phe Val
            340                 345                 350

Asp Asn His Asp Thr Gln Pro Gly Gln Ser Leu Glu Ser Thr Val Gln
        355                 360                 365

Thr Trp Phe Lys Pro Leu Ala Tyr Ala Phe Ile Leu Thr Arg Glu Ser
    370                 375                 380

Gly Tyr Pro Gln Val Phe Tyr Gly Asp Met Tyr Gly Thr Lys Gly Asp
385                 390                 395                 400

Ser Gln Arg Glu Ile Pro Ala Leu Lys His Lys Ile Glu Pro Ile Leu
                405                 410                 415

Lys Ala Arg Lys Gln Tyr Ala Tyr Gly Ala Gln His Asp Tyr Phe Asp
            420                 425                 430

His His Asp Ile Val Gly Trp Thr Arg Glu Gly Asp Ser Ser Val Ala
        435                 440                 445

Asn Ser Gly Leu Ala Ala Leu Ile Thr Asp Gly Pro Gly Gly Ala Lys
    450                 455                 460

Arg Met Tyr Val Gly Arg Gln Asn Ala Gly Glu Thr Trp His Asp Ile
465                 470                 475                 480

Thr Gly Asn Arg Ser Glu Pro Val Val Ile Asn Ser Glu Gly Trp Gly
                485                 490                 495

Glu Phe His Val Asn Gly Gly Ser Val Ser Ile Tyr Val Gln Arg
            500                 505                 510

(2) INFORMATION FOR SEQ ID NO: 36:

(i) SEQUENCE CHARACTERISTICS:
        (A) LENGTH: 520 amino acids
        (B) TYPE: amino acid
        (C) STRANDEDNESS: single -continued (D) TOPOLOGY: unknown (ii) MOLECULE TYPE: protein (xi) SEQUENCE DESCRIPTION: SEQ ID NO: 36:

```
Met Arg Gly Arg Gly Asn Met Ile Gln Lys Arg Lys Arg Thr Val Ser
1               5                   10                  15

Phe Arg Leu Val Leu Met Cys Thr Leu Leu Phe Val Ser Leu Pro Ile
            20                  25                  30

Thr Lys Thr Ser Ala Val Asn Gly Thr Leu Met Gln Tyr Phe Glu Trp
        35                  40                  45

Tyr Thr Pro Asn Asp Gly Gln His Trp Lys Arg Leu Gln Asn Asp Ala
    50                  55                  60

Glu His Leu Ser Asp Ile Gly Ile Thr Ala Val Trp Ile Pro Pro Ala
65                  70                  75                  80

Tyr Lys Gly Leu Ser Gln Ser Asp Asn Gly Tyr Gly Pro Tyr Asp Leu
                85                  90                  95

Tyr Asp Leu Gly Glu Phe Gln Gln Lys Gly Thr Val Arg Thr Lys Tyr
            100                 105                 110

Gly Thr Lys Ser Glu Leu Gln Asp Ala Ile Gly Ser Leu His Ser Arg
        115                 120                 125

Asn Val Gln Val Tyr Gly Asp Val Val Leu Asn His Lys Ala Gly Ala
    130                 135                 140

Asp Ala Thr Glu Asp Val Thr Ala Val Glu Val Asn Pro Ala Asn Arg
145                 150                 155                 160

Asn Gln Glu Thr Ser Glu Glu Tyr Gln Ile Lys Ala Trp Thr Asp Phe
                165                 170                 175

Arg Phe Pro Gly Arg Gly Asn Thr Tyr Ser Asp Phe Lys Trp His Trp
            180                 185                 190

Tyr His Phe Asp Gly Ala Asp Trp Asp Glu Ser Arg Lys Ile Ser Arg
        195                 200                 205

Ile Phe Lys Phe Arg Gly Glu Gly Lys Ala Trp Asp Trp Glu Val Ser
    210                 215                 220

Ser Glu Asn Gly Asn Tyr Asp Tyr Leu Met Tyr Ala Asp Val Asp Tyr
225                 230                 235                 240

Asp His Pro Asp Val Val Ala Glu Thr Lys Lys Trp Gly Ile Trp Tyr
                245                 250                 255

Ala Asn Glu Leu Ser Leu Asp Gly Phe Arg Ile Asp Ala Ala Lys His
            260                 265                 270

Ile Lys Phe Ser Phe Leu Arg Asp Trp Val Gln Ala Val Arg Gln Ala
        275                 280                 285

Thr Gly Lys Glu Met Phe Thr Val Ala Glu Tyr Trp Gln Asn Asn Ala
    290                 295                 300

Gly Lys Leu Glu Asn Tyr Leu Asn Lys Thr Ser Phe Asn Gln Ser Val
305                 310                 315                 320

Phe Asp Val Pro Leu His Phe Asn Leu Gln Ala Ala Ser Ser Gln Gly
                325                 330                 335

Gly Gly Tyr Asp Met Arg Arg Leu Leu Asp Gly Thr Val Val Ser Arg
            340                 345                 350

His Pro Glu Lys Ala Val Thr Phe Val Glu Asn His Asp Thr Gln Pro
        355                 360                 365

Gly Gln Ser Leu Glu Ser Thr Val Gln Thr Trp Phe Lys Pro Leu Ala
    370                 375                 380

Tyr Ala Phe Ile Leu Thr Arg Glu Ser Gly Tyr Pro Gln Val Phe Tyr
385                 390                 395                 400
```

```
Gly Asp Met Tyr Gly Thr Lys Gly Thr Ser Pro Lys Glu Ile Pro Ser
                405                 410                 415

Leu Lys Asp Asn Ile Glu Pro Ile Leu Lys Ala Arg Lys Glu Tyr Ala
                420                 425                 430

Tyr Gly Pro Gln His Asp Tyr Ile Asp His Pro Asp Val Ile Gly Trp
                435                 440                 445

Thr Arg Glu Gly Asp Ser Ser Ala Ala Lys Ser Gly Leu Ala Ala Leu
450                 455                 460

Ile Thr Asp Gly Pro Gly Gly Ser Lys Arg Met Tyr Ala Gly Leu Lys
465                 470                 475                 480

Asn Ala Gly Glu Thr Trp Tyr Asp Ile Thr Gly Asn Arg Ser Asp Thr
                485                 490                 495

Val Lys Ile Gly Ser Asp Gly Trp Gly Glu Phe His Val Asn Asp Gly
                500                 505                 510

Ser Val Ser Ile Tyr Val Gln Lys
                515                 520
```

(2) INFORMATION FOR SEQ ID NO: 37:

(i) SEQUENCE CHARACTERISTICS:
        (A) LENGTH: 548 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 37:

```
Val Leu Thr Phe His Arg Ile Ile Arg Lys Gly Trp Met Phe Leu Leu
1                   5                   10                  15

Ala Phe Leu Leu Thr Ala Ser Leu Phe Cys Pro Thr Gly Arg His Ala
                20                  25                  30

Lys Ala Ala Ala Pro Phe Asn Gly Thr Met Met Gln Tyr Phe Glu Trp
                35                  40                  45

Tyr Leu Pro Asp Asp Gly Thr Leu Trp Thr Lys Val Ala Asn Glu Ala
50                  55                  60

Asn Asn Leu Ser Ser Leu Gly Ile Thr Ala Leu Ser Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
                100                 105                 110

Gly Thr Lys Ala Gln Tyr Leu Gln Ala Ile Gln Ala Ala His Ala Ala
                115                 120                 125

Gly Met Gln Val Tyr Ala Asp Val Val Phe Asp His Lys Gly Gly Ala
130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
                180                 185                 190

Tyr His Phe Asp Gly Val Asp Trp Asp Glu Ser Arg Lys Leu Ser Arg
                195                 200                 205

Ile Tyr Lys Phe Arg Gly Ile Gly Lys Ala Trp Asp Trp Glu Val Asp
210                 215                 220
```

```
Thr Glu Asn Gly Asn Tyr Asp Tyr Leu Met Tyr Ala Asp Leu Asp Met
225                 230                 235                 240

Asp His Pro Glu Val Val Thr Glu Leu Lys Asn Trp Gly Lys Trp Tyr
            245                 250                 255

Val Asn Thr Thr Asn Ile Asp Gly Phe Arg Leu Asp Gly Leu Lys His
            260                 265                 270

Ile Lys Phe Ser Phe Phe Pro Asp Trp Leu Ser Tyr Val Arg Ser Gln
        275                 280                 285

Thr Gly Lys Pro Leu Phe Thr Val Gly Glu Tyr Trp Ser Tyr Asp Ile
        290                 295                 300

Asn Lys Leu His Asn Tyr Ile Thr Lys Thr Asn Gly Thr Met Ser Leu
305                 310                 315                 320

Phe Asp Ala Pro Leu His Asn Lys Phe Tyr Thr Ala Ser Lys Ser Gly
            325                 330                 335

Gly Ala Phe Asp Met Arg Thr Leu Met Thr Asn Thr Leu Met Lys Asp
            340                 345                 350

Gln Pro Thr Leu Ala Val Thr Phe Val Asp Asn His Asp Thr Asn Pro
        355                 360                 365

Ala Lys Arg Cys Ser His Gly Arg Pro Trp Phe Lys Pro Leu Ala Tyr
        370                 375                 380

Ala Phe Ile Leu Thr Arg Gln Glu Gly Tyr Pro Cys Val Phe Tyr Gly
385                 390                 395                 400

Asp Tyr Tyr Gly Ile Pro Gln Tyr Asn Ile Pro Ser Leu Lys Ser Lys
            405                 410                 415

Ile Asp Pro Leu Leu Ile Ala Arg Arg Asp Tyr Ala Tyr Gly Thr Gln
            420                 425                 430

His Asp Tyr Leu Asp His Ser Asp Ile Ile Gly Trp Thr Arg Glu Gly
        435                 440                 445

Val Thr Glu Lys Pro Gly Ser Gly Leu Ala Ala Leu Ile Thr Asp Gly
        450                 455                 460

Ala Gly Arg Ser Lys Trp Met Tyr Val Gly Lys Gln His Ala Gly Lys
465                 470                 475                 480

Val Phe Tyr Asp Leu Thr Gly Asn Arg Ser Asp Thr Val Thr Ile Asn
            485                 490                 495

Ser Asp Gly Trp Gly Glu Phe Lys Val Asn Gly Gly Ser Val Ser Val
            500                 505                 510

Trp Val Pro Arg Lys Thr Thr Val Ser Thr Ile Ala Arg Pro Ile Thr
        515                 520                 525

Thr Arg Pro Trp Thr Gly Glu Phe Val Arg Trp His Glu Pro Arg Leu
        530                 535                 540

Val Ala Trp Pro
545
```

(2) INFORMATION FOR SEQ ID NO: 38:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Met Lys Gln Gln Lys Arg Leu Thr Ala Arg Leu Leu Thr Leu Leu Phe
1               5                   10                  15

Ala Leu Ile Phe Leu Leu Pro His Ser Ala Ala Ala Ala Ala Asn Leu
```

```
                      20                  25                  30

(2) INFORMATION FOR SEQ ID NO: 39:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
                20                  25                  30

Ser (2) INFORMATION FOR SEQ ID NO: 40:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Asn Leu
                20                  25                  30
```

We claim:

1. An α-amylase that is the expression product of a mutated DNA sequence encoding an α-amylase, the mutated DNA sequence being derived from a precursor α-amylase by substitution corresponding to N188T.

2. The α-amylase according to claim 1, wherein said substitution or substitution further comprises the deletion or substitution of a methionine or tryptophan residue.

3. The α-amylase according to claim 2, wherein said substitution or substitution of said methionine or tryptophan residue comprises a substitution or deletion corresponding to M15, W138 or M197 in *Bacillus licheniformis*.

4. The α-amylase according to claim 1 wherein said substitution or substitution further comprises the deletion or substitution of a residue corresponding to V129, H133, S187 or A209 in *Bacillus licheniformis*.

5. An α-amylase that is the expression product of a mutated DNA sequence encoding an α-amylase, the mutated DNA sequence being derived from a precursor α-amylase by a substitution corresponding to M15T/N188S, M15L/N188S, M15T/H133Y/N188S, M15T/H133Y/N188S/A209V, M15T/N188S/A209V, M15T/V128E/H133Y/N188S, M15T/S187D/N188S, M15T/N188T, M15L/N188T, M15T/H133Y/N188T, M15T/H133Y/N188T/A209V, M15T/N188T/A209V. M15T/V128E/H133Y/N188T, M15T/S187D/N188T in *Bacillus licheniformis*.

6. The α-amylase according to claim 3, wherein said substitution of said methionine residues comprises a substitution corresponding to M15T, W138Y or M197T in *Bacillus licheniformis*.

7. The α-amylase according to claim 1, wherein said precursor α-amylase is derived from Bacillus.

8. The α-amylase according to claim 7, wherein said precursor α-amylase is derived from *Bacillus licheniformis*.

9. A DNA encoding the α-amylase according to claim 1.

10. A DNA encoding the α-amylase according to claim 3.

11. A DNA encoding the α-amylase according to claim 4.

12. A DNA encoding the α-amylase according to claim 5.

13. An expression vector comprising the DNA of claim 9.

14. An expression vector comprising the DNA of claim 10.

15. An expression vector comprising the DNA of claim 11.

16. An expression vector comprising the DNA of claim 12.

17. A host cell transformed with the expression vector of claim 13.

18. A host cell transformed with the expression vector of claim 14.

19. A host cell transformed with the expression vector of claim 15.

20. A host cell transformed with the expression vector of claim 16.

21. An α-amylase according to claims 1, 4 or 5 having enhanced low pH performance.

22. A detergent composition comprising the α-amylase according to claims 1, 4 or 5.

23. The detergent composition according to claim 22, wherein said detergent is useful in laundering soiled fabric.

24. The detergent composition according to claim 22, wherein said detergent is useful in washing soiled dishes.

25. A method of liquefying starch comprising the steps of:
(a) preparing a solution comprising starch polymer;
(b) combining with said solution of starch polymer the α-amylase according to claim 1 under conditions and for a time suitable to liquefy said starch polymer.

26. The method of claim 25, wherein said α-amylase comprises the α-amylase according to claim 2.

27. The method of claim 25, wherein said α-amylase comprises the α-amylase according to claim 3.

28. The method of claim 25, wherein said α-amylase comprises the α-amylase according to claim 4.

29. The method of claim 25, wherein said α-amylase comprises the α-amylase according to claim 5.

30. The method of claim 25, wherein said α-amylase comprises the α-amylase according to claim 6.

31. The method of claim 25, wherein said α-amylase comprises the α-amylase according to claim 7.

32. The method of claim 25, wherein said α-amylase comprises the α-amylase according to claim 8.

* * * * *

UNITED STATES PATENT AND TRADEMARK OFFICE
CERTIFICATE OF CORRECTION

PATENT NO. : 5,958,739
DATED : September 28, 1999
INVENTOR(S) : Colin Mitchinson et al.

It is certified that error appears in the above-identified patent and that said Letters Patent is hereby corrected as shown below:

The attached Sequence listings should be added to the sequence listing disk.

Signed and Sealed this

Seventeenth Day of August, 2004

JON W. DUDAS
*Acting Director of the United States Patent and Trademark Office*

(2) INFORMATION FOR SEQ ID NO: 41:

(i) SEQUENCE CHARACTERISTICS:
    (A) LENGTH: 512 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO: 41:

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Ala Asn Leu
        20                  25                  30

Asn Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
        50                  55                  60

Gly Ile Thr Ala Val Trp Ile Pro Pro Ala Tyr Lys Gly Thr Ser Gln
 65              70                  75                  80

Ala Asp Val Gly Tyr Gly Ala Tyr Asp Leu Tyr Asp Leu Gly Glu Phe
        85                  90                  95

His Gln Lys Gly Thr Val Arg Thr Lys Tyr Gly Thr Lys Gly Glu Leu
        100                 105                 110

Gln Ser Ala Ile Lys Ser Leu His Ser Arg Asp Ile Asn Val Tyr Gly
        115                 120                 125
```

Asp Val Val Ile Asn His Lys Gly Gly Ala Asp Ala Thr Glu Asp Val
    130             135            140

Thr Ala Val Glu Val Asp Pro Ala Asp Arg Asn Arg Val Ile Ser Gly
145          150          155          160

Glu His Leu Ile Lys Ala Trp Thr His Phe His Phe Pro Gly Arg Gly
       165          170         175

Ser Thr Tyr Ser Asp Phe Lys Trp His Trp Tyr His Phe Asp Gly Thr
    180           185         190

Asp Trp Asp Glu Ser Arg Lys Leu Asn Arg Ile Tyr Lys Phe Gln Gly
   195          200         205

Lys Ala Trp Asp Trp Glu Val Ser Asn Glu Asn Gly Asn Tyr Asp Tyr
   210          215         220

Leu Met Tyr Ala Asp Ile Asp Tyr Asp His Pro Asp Val Ala Ala Glu
225          230          235         240

Ile Lys Arg Trp Gly Thr Trp Tyr Ala Asn Glu Leu Gln Leu Asp Gly
    245         250          255

Phe Arg Leu Asp Ala Val Lys His Ile Lys Phe Ser Phe Leu Arg Asp
    260         265         270

Trp Val Asn His Val Arg Glu Lys Thr Gly Lys Glu Met Phe Thr Val
   275          280         285

Ala Glu Tyr Trp Gln Asn Asp Leu Gly Ala Leu Glu Asn Tyr Leu Asn
  290         295         300

Lys Thr Asn Phe Asn His Ser Val Phe Asp Val Pro Leu His Tyr Gln
305          310         315         320

Phe His Ala Ala Ser Thr Gln Gly Gly Gly Tyr Asp Met Arg Lys Leu
     325         330         335

Leu Asn Gly Thr Val Val Ser Lys His Pro Leu Lys Ser Val Thr Phe
    340         345         350

Val Asp Asn His Asp Thr Gln Pro Gly Gln Ser Leu Glu Ser Thr Val
    355         360         365

Gln Thr Trp Phe Lys Pro Leu Ala Tyr Ala Phe Ile Leu Thr Arg Glu
    370         375         380

Ser Gly Tyr Pro Gln Val Phe Tyr Gly Asp Met Tyr Gly Thr Lys Gly
385          390         395         400

Asp Ser Gln Arg Glu Ile Pro Ala Leu Lys His Lys Ile Glu Pro Ile
        405             410             415

Leu Lys Ala Arg Lys Gln Tyr Ala Tyr Gly Ala Gln His Asp Tyr Phe
        420             425         430

Asp His His Asp Ile Val Gly Trp Thr Arg Glu Gly Asp Ser Ser Val
        435             440         445

Ala Asn Ser Gly Leu Ala Ala Leu Ile Thr Asp Gly Pro Gly Gly Ala
    450             455         460

Lys Arg Met Tyr Val Gly Arg Gln Asn Ala Gly Glu Thr Trp His Asp
465             470         475             480

Ile Thr Gly Asn Arg Ser Glu Pro Val Val Ile Asn Ser Glu Gly Trp
        485             490         495

Gly Glu Phe His Val Asn Gly Gly Ser Val Ser Ile Tyr Val Gln Arg
        500         505         510